US012662468B2

(12) United States Patent
Sythana et al.

(10) Patent No.: US 12,662,468 B2
(45) Date of Patent: Jun. 23, 2026

(54) PROCESS FOR THE SYNTHESIS OF ANTHRANILIC ACID/AMIDE COMPOUNDS AND INTERMEDIATES THEREOF

(71) Applicant: PI INDUSTRIES LIMITED, Udaipur-Rajasthan (IN)

(72) Inventors: Suresh Kumar Sythana, Hyderabad (IN); Pramod Nagle, Jalgaon (IN); Vijay Kumar Kumar, Udaipur (IN); Shrikant Bhausaheb Kanawade, Nashik (IN); Tukaram Nivrutti Chandre, Nashik Maharashtra (IN); Vinayak Kisan Thube, Ahmednagar Maharashtra (IN); Pradeep Prakash Patil, Jalgaon (IN); Shalini Shukla, Udaipur (IN); Kantilal Balu Shende, Ahmednagar (IN); Pranab Kumar Patra, Udaipur (IN); Alexander G.M. Klausener, Pulheim (DE)

(73) Assignee: PI INDUSTRIES LIMITED, Udaipur-Rajasthan (IN)

( * ) Notice: Subject to any disclaimer, the term of this patent is extended or adjusted under 35 U.S.C. 154(b) by 539 days.

(21) Appl. No.: 18/028,001

(22) PCT Filed: Sep. 25, 2021

(86) PCT No.: PCT/IB2021/058749

§ 371 (c)(1),
(2) Date: Mar. 23, 2023

(87) PCT Pub. No.: WO2022/064454

PCT Pub. Date: Mar. 31, 2022

(65) Prior Publication Data

US 2023/0339906 A1 Oct. 26, 2023

(30) Foreign Application Priority Data

Sep. 26, 2020 (IN) ............................. 202011041843

(51) Int. Cl.

| | |
|---|---|
| ***C07D 403/04*** | (2006.01) |
| ***B01J 27/057*** | (2006.01) |
| ***C07C 227/18*** | (2006.01) |
| ***C07C 233/15*** | (2006.01) |

(52) U.S. Cl.

CPC ........ *C07D 403/04* (2013.01); *B01J 27/0573* (2013.01); *C07C 227/18* (2013.01); *C07C 233/15* (2013.01)

(58) Field of Classification Search

CPC .. C07D 403/04; C07D 209/38; C07D 401/04; B01J 27/0573; C07C 227/18; C07C 233/15; C07C 2601/02; C07C 231/02; C07C 231/12; C07C 249/06; C07C 253/20; C07C 229/26; C07C 233/56; C07C 237/30; C07C 251/40; C07C 255/00; C07C 291/00

See application file for complete search history.

(56) References Cited

U.S. PATENT DOCUMENTS

| | | | |
|---|---|---|---|
| 2007/0299265 A1 | 12/2007 | Shapiro et al. | |
| 2009/0306372 A1 | 12/2009 | Davis et al. | |

FOREIGN PATENT DOCUMENTS

| | | | |
|---|---|---|---|
| WO | WO-2006062978 A1 * | 6/2006 | ........... C07D 231/20 |
| WO | 2008010897 A1 | 1/2008 | |
| WO | WO-2008010897 A2 * | 1/2008 | ........... C07D 231/16 |
| WO | WO-2020170092 A1 * | 8/2020 | ........... C07D 403/06 |

OTHER PUBLICATIONS

Silva Joaquim et al, "The chemistry of isatins: a review from 1975 to 1999", São Paulo; BR Jun. 1, 2001 (Jun. 1, 2001), vol. 12, No. 3, p. 273-324, Retrieved from the Internet: URL:https://www.scielo.br/j/jbchs/a/DJcvtMb8RHxnF8jcMLqQJtk/?format=pdf&lang=enXP055878002; DOI: 10.1590/S0103-50532001000300002 external link ISSN:0103-5053.

* cited by examiner

*Primary Examiner* — Deborah D Carr
(74) *Attorney, Agent, or Firm* — Lippes Mathias LLP

(57) ABSTRACT

The present invention discloses a process for the synthesis of compound of formula (VII) or a salt thereof, (VII)

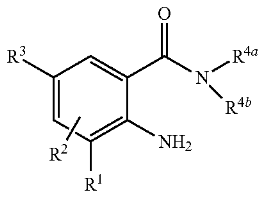

wherein, R, $R^1$, $R^2$, $R^3$, $R^{4a}$ and $R^{4b}$ are as defined in the detailed description. The process further comprises the synthesis of an anthranilic diamide compound of formula (I).

23 Claims, No Drawings

PROCESS FOR THE SYNTHESIS OF ANTHRANILIC ACID/AMIDE COMPOUNDS AND INTERMEDIATES THEREOF

This application is a National Stage Entry of International Application No. PCT/IB2021/058749, filed Sep. 25, 2021, which claims priority to Indian Application No. 202011041843, filed Sep. 26, 2020, the contents of which are incorporated by reference herein.

FIELD OF THE INVENTION

The present invention relates to a process for the synthesis of a compound of formula (VII) or a salt thereof. Further the present invention comprises a process for the synthesis of anthranilic diamides of formula (I) from substituted anilines of formula (II), making use of compounds of formula (VII).

BACKGROUND OF THE INVENTION

WO2003015518, WO2003015519, WO2004067528, WO2005077934 and WO20100069502 disclose the use of anthranilic acid diamides for controlling invertebrate pests such as arthropods.

Several patent documents, for example WO2004011447, WO2004111030, WO2006062978, WO2008010897 and WO2012103436 disclose processes for preparing anthranilic diamides and suitable intermediates.

Russian Journal of Organic Chemistry, 2019, vol. 55, 4, p. 540-545 reports the synthesis of oxime derivatives falling under the definition of formula (IV).

However, the selectivity towards the formation of such oxime products is not satisfactory. In this process, dimethyl sulfoxide is used as a solvent as well as an oxidising agent and gives finally better results. However, on production scale, the use of this solvent is not economical, since specifically solvent recovery is not possible due to instability of the oxime at higher temperature. Also, excess volume of water is often required to quench the reaction rendering the operation throughput lower. The said issue has now been addressed in the present invention wherein the use of DMSO to obtain the desired oxime is avoided.

The conversion of isatin derivatives to isatoic anhydrides is well known in the prior art. However, the reaction, if following the procedures that are described in the state of the art, are not going to completion at larger scale.

N-substituted anthranilic amides with desired substitution patterns being suitable as advanced intermediates for the preparation of anthranilic acid diamides of formula (I), are not easily available, and processes mentioned in the literatures to synthesize them lack from selectivity as well as from scalability. Therefore, there is a need to find a simple, efficient and industrially economical process for the preparation of anthranilic acid diamides of formula (I) from N-substituted anthranilic amides of formula (VII) as well as for N-substituted anthranilic amides of formula (VII) themselves. This need is addressed by the present invention.

OBJECTIVE OF THE INVENTION

The objective of the present invention is to provide a process for the synthesis of N-substituted anthranilic amides of formula (VII).

Another objective of the present invention is to provide a process for the synthesis of compounds of formula (IV) and compounds of formula (V).

Yet another objective of the present invention is to provide a simple, environment-friendly and cost-effective process for the synthesis of anthranilic diamides of formula (I), based on readily available starting materials.

SUMMARY OF THE INVENTION

It is the objective of the present invention to provide an industrially amenable and convenient process for the preparation of anthranilic amides of formula (VII).

Surprisingly, the present invention provides a solution to this objective by providing a novel process that allows the preparation of anthranilic amides, overcoming at least one of the shortcomings of the processes described in the prior art.

Accordingly, the present invention provides a novel process for preparing a compound of formula (VII), (VII)

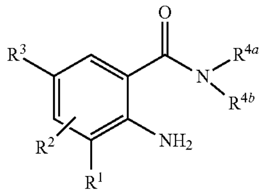

wherein, $R^1$ is selected from the group comprising of halogen, $C_1$-$C_4$ alkyl, $C_1$-$C_4$ haloalkyl and $C_3$-$C_4$-cycloalkyl;

$R^2$ is selected from the group comprising of hydrogen, halogen, cyano, $C_1$-$C_4$ alkyl and $C_3$-$C_4$-cycloalkyl;

$R^3$ is selected from the group comprising of hydrogen, halogen, cyano, $C_1$-$C_4$ haloalkyl or $C_3$-$C_6$ cycloalkyl;

$R^{4a}$ and $R^{4b}$ are independently selected from the group comprising of hydrogen, $C_1$-$C_6$ alkyl, $C_3$-$C_6$ cycloalkyl, $C_3$-$C_6$ cycloalkyl-$C_1$-$C_4$ alkyl; or $NR^{4a}R^{4b}$ represent —N═S($R^7R^8$)═(O)$_n$; wherein $R^7$ and $R^8$ are independently selected from the group comprising of $C_1$-$C_4$ alkyl, $C_1$-$C_4$ haloalkyl $C_3$-$C_6$ cycloalkyl or $C_3$-$C_6$ cycloalkyl $C_1$-$C_4$ alkyl and n stands for 0, or 1 comprising the steps of:

a) reacting the compound of formula (II) with the compound of formula (III) to afford a compound of formula (IV), optionally in the presence of a suitable base and a solvent;

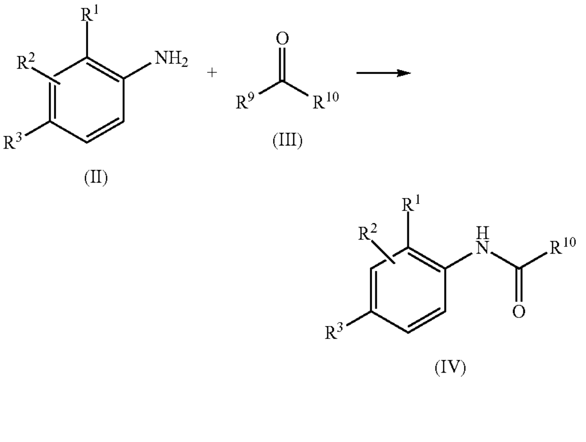

(II) (III) (IV)

wherein, $R^1$, $R^2$ and $R^3$ are defined herein above;

$R^9$ is selected from the group comprising of Cl, Br or $C_1$-$C_4$ alkoxy;

$R^{10}$ is selected from the group comprising of cyano, $CH_2X$, $CH_2$—(C═O)—$OR^a$, $CH_2$—(C═O)—$NHR^f$, $COOR^a$, $C(O)R^c$ or $CR^d$═$NR^e$;

$R^a$ is selected from the group comprising of hydrogen or $C_1$-$C_4$-alkyl, $R^c$ is selected from the group comprising of $N(R^a)_2$ or two $R^a$ of $N(R^a)_2$ group together with the atoms to which they are attached or together with further atoms selected from the group consisting of C, N, O, S and optionally including 1 to 3 ring members selected from the group consisting of C(═O), C(═S), $S(O)_m$ and $SiR'_2$ may form a five to six membered non-aromatic ring;

$R^d$ is selected from the groups comprising of hydrogen and $C_1$-$C_4$-alkyl, (C═O)—$R^a$, $COOR^a$, $CON(R^a)_2$ and phenyl;

$R^e$ is selected from the groups comprising of hydroxy and $C_1$-$C_4$ alkoxy;

$R^f$ is selected from the groups comprising of optionally substituted phenyl, wherein substitution is selected from group comprising of halogen or $C_1$-$C_4$-alkyl;

X represents halogen;

b) reacting the compound of formula (IV) with a suitable acid to obtain isatin of formula (V), optionally in the presence of a suitable solvent;

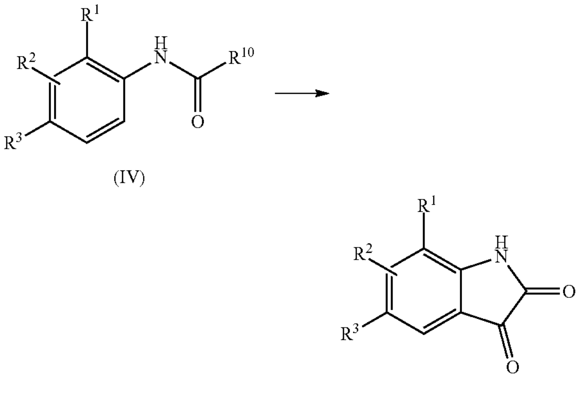

(IV)

(V)

wherein, $R^1$, $R^2$, $R^3$ and $R^{10}$ have same meaning as define above;

c) oxidizing the isatin of formula (V) to obtain an isatoic anhydride of formula (VI) in the presence of a suitable oxidizing agent and a suitable catalyst, optionally in the presence of a suitable solvent;

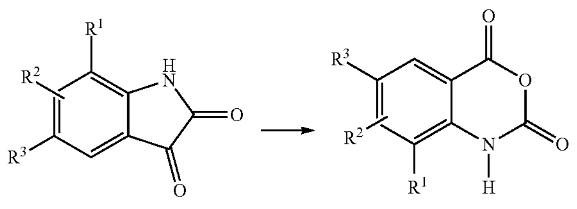

(V) (VI)

wherein, $R^1$, $R^2$, and $R^3$ have the same meaning as defined above;

or hydrolyzing the isatin of formula (V) to obtain an anthranilic acid of formula (VIIa) in the presence of a suitable hydrolyzing agent, optionally in the presence of a suitable solvent;

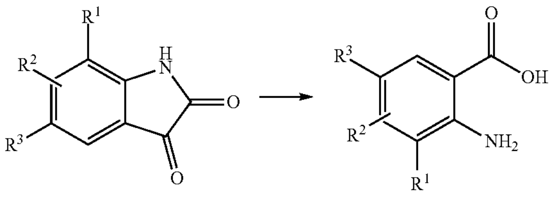

(V) (VIIa)

wherein, $R^1$, $R^2$, and $R^3$ have the same meaning as defined above;

d) reacting the compound of formula (VI) with a compound of formula (VIII), to obtain a compound of Formula (VII), optionally in the presence of a suitable acid and a suitable solvent; as shown in the following scheme:

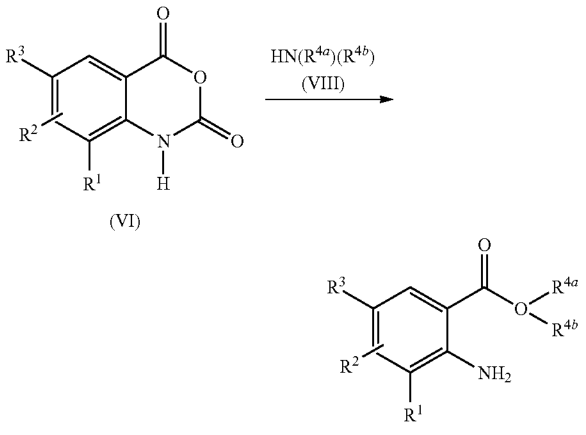

(VI)

(VII)

$R^1$, $R^2$, $R^3$, $R^{4a}$ and $R^{4b}$ wherein have same meaning as define above;

Furthermore, the present invention provides a process for the synthesis of anthranilic diamides of formula (I), Formula (I)

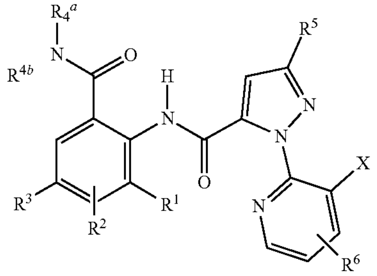

wherein, $R^1$ is selected from the group comprising of halogen, $C_1$-$C_4$ alkyl, $C_1$-$C_4$ haloalkyl and $C_3$-$C_4$-cycloalkyl;

$R^2$ is selected from the group comprising of hydrogen, halogen, cyano, $C_1$-$C_4$ alkyl and $C_3$-$C_4$-cycloalkyl;

$R^3$ is selected from the group comprising of hydrogen, halogen, cyano, $C_1$-$C_4$ haloalkyl or $C_3$-$C_6$ cycloalkyl;

$R^{4a}$ and $R^{4b}$ are independently selected from the group comprising of hydrogen, $C_1$-$C_4$ alkyl, $C_3$-$C_6$ cycloalkyl, $C_3$-$C_6$ cycloalkyl-$C_1$-$C_4$ alkyl; or $NR^{4a}R^{4b}$ represents —N═S($R^7R^8$)═(O)$_n$; wherein $R^7$ and $R^8$ are independently selected from the group comprising of $C_1$-$C_4$ alkyl, $C_1$-$C_4$ haloalkyl $C_3$-$C_6$ cycloalkyl or $C_3$-$C_6$ cycloalkyl $C_1$-$C_4$ alkyl;

n represents an integer from 0-1;

$R^5$ is selected from the group comprising of halogen, $C_1$-$C_4$ alkyl, $C_1$-$C_4$ haloalkyl, $CHF_2$, $CF_3$, $C_1$-$C_4$ alkoxy; $OCF_2H$, $OCH_2CF_3$, or -A-$C_3$-$C_5$ heterocyclyl;

wherein -A- is selected from the group comprising of direct bond, $CHR^6$, —O— or —S—; and said heterocyclyl may optionally be substituted with one or more group selected from hydrogen, halogen, cyano, $C_1$-$C_4$ alkyl or $C_1$-$C_4$ haloalkyl;

$R^6$ is selected from the group comprising of hydrogen, halogen, cyano, $C_1$-$C_4$ alkyl or $C_1$-$C_4$ haloalkyl;

X is halogen;

from a substituted anilines of formula (II);

II

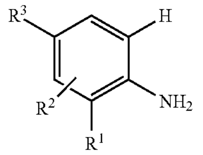

wherein, $R^1$ is selected from the group comprising of halogen, $C_1$-$C_4$ alkyl, $C_1$-$C_4$ haloalkyl and $C_3$-$C_4$-cycloalkyl;

$R^2$ is selected from the group comprising of hydrogen, halogen, cyano, $C_1$-$C_4$ alkyl and $C_3$-$C_4$-cycloalkyl;

$R^3$ is selected from the group comprising of hydrogen, halogen, cyano, $C_1$-$C_4$ haloalkyl or $C_3$-$C_6$ cycloalkyl;

according to the reaction scheme as depicted below,

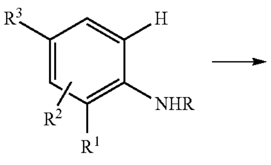

II

-continued

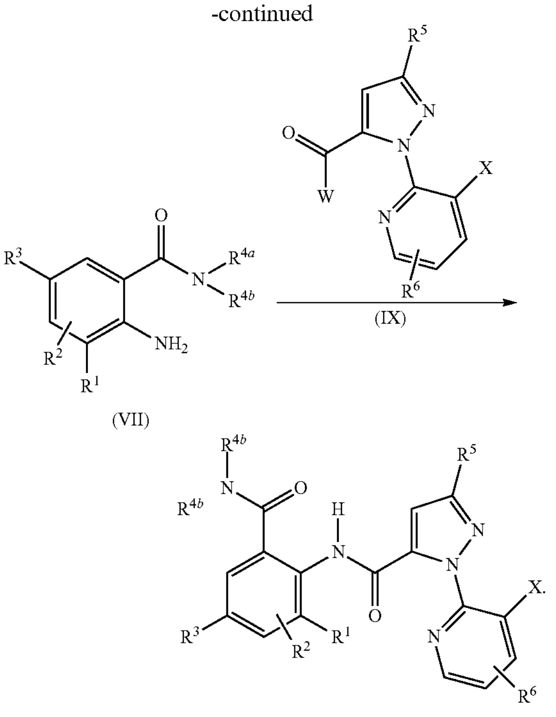

(VII)

I wherein W is OH, Cl, O—$C_1$-$C_4$ alkyl, O—C(O)$C_1$-$C_4$ alkyl or imidazolyl; $R^1$, $R^2$, $R^3$, $R^{4a}$, $R^{4b}$, $R^5$, $R^6$ and X have the same meaning as defined above.

DETAILED DESCRIPTION OF THE INVENTION

General Definitions

The definitions provided herein for the terminologies used in the present disclosure are for illustrative purpose only and in no manner limit the scope of the present invention disclosed in the present disclosure.

As used herein, the terms “comprises”, “comprising”, “includes”, “including”, “has”, “having”, “contains”, “containing”, “characterized by” or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase “consisting of” excludes any element, step or ingredient not specified. If in the claim, such would close the claim to the inclusion of materials other than those recited except for impurities ordinarily associated therewith. When the phrase “consisting of” appears in a clause of the body of a claim, rather than immediately following the preamble, it limits only the element set forth in that clause; other elements are not excluded from the claim as a whole.

The transitional phrase “consisting essentially of” is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Further, unless expressly stated to the contrary, "or" refers to an inclusive "or" and not to an exclusive "or". For example, a condition A "or" B is satisfied by any one of the following: A is true (or present) and B is false (or not present), A is false (or not present) and B is true (or present), and both A and B are true (or present).

Also, the indefinite articles "a" and "an" preceding an element or component of the present invention are intended to be non-restrictive regarding the number of instances (i.e. occurrences) of the element or component. Therefore "a" or "an" should be read to include one or at least one, and the singular word form of the element or component also includes the plural unless the number is obviously meant to be singular.

Carbon-based radical refers to a monovalent molecular component comprising a carbon atom that connects the radical to the remainder of the chemical structure through a single bond. Carbon-based radicals can optionally comprise saturated, unsaturated and aromatic groups, chains, rings and ring systems, and heteroatoms. Although carbon-based radicals are not subject to any particular limit in size, in the context of the present invention they typically comprise 1 to 16 carbon atoms and o to 3 heteroatoms. Of note are carbon-based radicals selected from $C_1$-$C_6$ alkyl, $C_1$-$C_6$ haloalkyl and phenyl optionally substituted with 1-3 substituents selected from $C_1$-$C_3$ alkyl, halogen and nitro.

The meaning of various terms used in the description shall now be illustrated.

The term "alkyl", used either alone or in compound words such as "alkylthio" or "haloalkyl" or —N(alkyl) or alkylcarbonylalkyl or alkylsuphonylamino includes straight-chain or branched $C_1$ to $C_6$ alkyl. Representative examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or poly-substituted identically or differently and independently by alkyl. The same also applies to composite substituents in which other radicals, for example alkenyl, alkynyl, hydroxyl, halogen, carbonyl, carbonyloxy and the like, are at the end.

The term "cycloalkyl" means alkyl closed to form a ring. Representative examples include but are not limited to cyclopropyl, cyclobutyl, cyclopentyl and cyclohexyl. This definition also applies to cycloalkyl as a part of a composite substituent, for example cycloalkylalkyl etc., unless specifically defined elsewhere.

The term "alkoxy" used either alone or in compound words included $C_1$ to $C_6$ alkoxy. Non limiting examples of alkoxy include methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy a and 1-ethyl-2-methylpropoxy and the different isomers. This definition also applies to alkoxy as a part of a composite substituent, for example haloalkoxy, alkynylalkoxy, etc., unless specifically defined elsewhere.

The term "hydroxy" means —OH.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Non-limiting examples of "haloalkyl" include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1,1-dichloro-2,2,2-trifluoroethyl, and 1,1,1-trifluoroprop-2-yl. This definition also applies to haloalkyl as a part of a composite substituent, unless specifically defined elsewhere.

The term "hetero" in connection with rings refers to a ring in which at least one ring atom is not carbon and which can contain 1 to 4 heteroatoms independently selected from the group consisting of nitrogen, oxygen and sulfur, provided that each ring contains no more than 4 nitrogen, no more than 2 oxygen and no more than 2 sulfur.

The term "aromatic" indicates that the Huckel rule is satisfied and the term "non-aromatic" indicates that the Huckel rule is not satisfied.

The term "heterocycle" or "heterocyclic" or "heterocyclyl" includes "aromatic heterocycle" or "heteroaryl bicyclic ring system" and "nonaromatic heterocycle" or polycyclic or bicyclic (spiro, fused, bridged, non-fused) ring compounds in which ring may be aromatic or non-aromatic, wherein the heterocycle ring contains at least one heteroatom selected from N, O, $S(O)_{0-2}$, and/or C ring member of the heterocycle may be replaced by C(=O) and C(=S).

The term "non-aromatic heterocycle" or "non-aromatic heterocyclic" means three- to ten-membered, preferably three- to six-membered, saturated or partially unsaturated heterocycle containing one to four heteroatoms, selected from the group of oxygen, nitrogen and sulphur; mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxetanyl, thietanyl, oxiranyl, aziridinyl, azetidinyl, tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, oxadiazolidinyl, thiadiazolidinyl, triazolidinyl, dihydrofuryl, dihydrothienyl, pyrrolinyl, isoxazolinyl, isothiazolinyl, dihydropyrazolyl, dihydrooxazolyl, dihydrothiazolyl, piperidinyl, pyrazynyl, morpholinyl, thiomorphlinyl, 1,3-dioxany, tetrahydropyranyl, tetrahydrothienyl; wherein these rings are attached to the skeleton via one of the carbon or nitrogen of said rings. This definition also applies to heterocyclyl as a part of a composite substituent, for example heterocyclylalkyl etc., unless specifically defined elsewhere.

The term "heteroaryl" or "aromatic heterocyclic" means 5-membered, fully unsaturated monocyclic ring system containing one to four heteroatoms selected from the group of oxygen, nitrogen and sulphur; if the ring contains more than one oxygen atom, they are not directly adjacent; 5-membered heteroaryl containing one to four nitrogen atoms or one to three nitrogen atoms and one sulphur or oxygen atom; 5-membered heteroaryl groups which, in addition to carbon atoms, may contain one to four nitrogen atoms or one to three nitrogen atoms and one sulphur or oxygen atom as ring members, for example (but not limited thereto) furyl, thienyl, pyrrolyl, isoxazolyl, isothiazolyl, pyrazolyl, oxazolyl, thiazolyl, imidazolyl, oxadiazolyl, thiadiazolyl, triazolyl, tetrazolyl; wherein these rings are attached to the skeleton via one of the carbon or nitrogen of said rings, To achieve at least one of the above defined objectives, the present invention provides a process for the synthesis of compound of formula (VII).

In one aspect, the present invention provides a process for the synthesis of a compound of formula (VII) or a salt thereof, (VII)

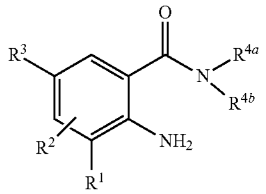

wherein, $R^1$ is selected from the group comprising of halogen, $C_1$-$C_4$ alkyl, $C_1$-$C_4$ haloalkyl and $C_3$-$C_4$-cycloalkyl;

$R^2$ is selected from the group comprising of hydrogen, halogen, cyano, $C_1$-$C_4$ alkyl and $C_3$-$C_4$-cycloalkyl;

$R^3$ is selected from the group comprising of hydrogen, halogen, cyano, $C_1$-$C_4$ haloalkyl or $C_3$-$C_6$ cycloalkyl;

$R^{4a}$ and $R^{4b}$ are independently selected from the group comprising of hydrogen, $C_1$-$C_6$ alkyl, $C_3$-$C_6$ cycloalkyl, $C_3$-$C_6$ cycloalkyl-$C_1$-$C_4$ alkyl; or $NR^{4a}R^{4b}$ represent —N═S($R^7R^8$)═(O)$_n$; wherein $R^7$ and $R^8$ are independently selected from the group comprising of $C_1$-$C_4$ alkyl, $C_1$-$C_4$ haloalkyl $C_3$-$C_6$ cycloalkyl or $C_3$-$C_6$ cycloalkyl $C_1$-$C_4$ alkyl and n stands for 0, or 1 comprising the steps of:

a) reacting the compound of formula (II) with a compound of formula (III) to afford a compound of formula (IV), optionally in the presence of a suitable base and a solvent;

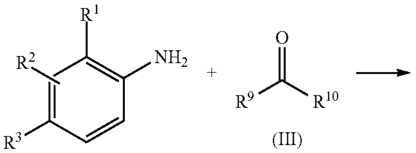

(II) (III)

-continued

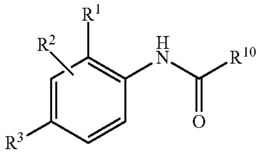

(IV)

wherein, $R^1$, $R^2$ and $R^3$ have the same meaning as defined above;

$R^9$ is selected from the group comprising of Cl, Br or $C_1$-$C_4$ alkoxy;

$R^{10}$ is selected from the group comprising of cyano, $CH_2X$, $CH_2$—(C═O)—$OR^a$, $CH_2$—(C═O)— $NHR^f$, $COOR^a$, C(O)$R^c$ or $CR^d$═$NR^e$;

$R^a$ is selected from the group comprising of hydrogen or $C_1$-$C_4$-alkyl, $R^c$ is selected from the group comprising of $N(R^a)_2$ or two $R^a$ together with the atoms to which they are attached or together with further atoms selected from the group consisting of C, N, O, S and optionally including 1 to 3 ring members selected from the group consisting of C(═O), C(═), $S(O)_m$ and $SiR'_2$ may form a five to six membered non-aromatic ring;

$R^d$ is selected from the groups comprising of hydrogen and $C_1$-$C_4$-alkyl, (C═O)—$R^a$, $COOR^a$, $CON(R^a)_2$ and phenyl;

$R^e$ is selected from the groups comprising of hydroxy and $C_1$-$C_4$ alkoxy;

$R^f$ is selected from the groups comprising of optionally substituted phenyl, wherein substitution is selected from group comprising of halogen or $C_1$-$C_4$-alkyl;

X represents halogen;

b) reacting the compound of formula (IV) with a suitable acid to obtain an isatin of formula (V), optionally in the presence of a suitable solvent;

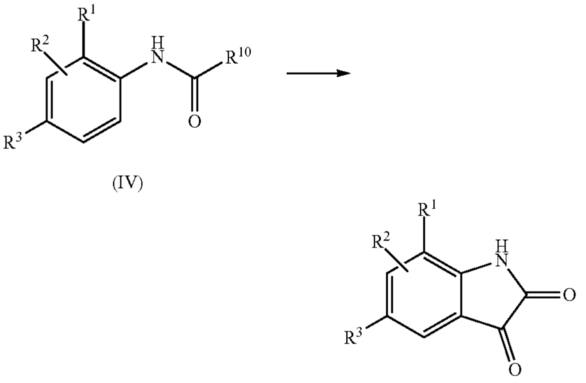

(IV)

(V)

wherein, $R^1$, $R^2$, $R^3$ and $R^{10}$ have same meaning as defined above;

c) oxidizing the isatin of formula (V) to obtain an isatoic anhydride of formula (VI) in the presence of a suitable oxidizing agent and a suitable catalyst, optionally in the presence of a suitable solvent;

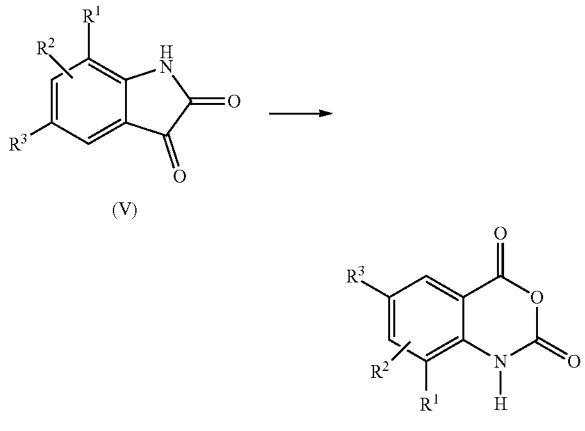

(V)

(VI)

wherein, $R^1$, $R^2$, and $R^3$ have the same meaning as defined above;

d) reacting the compound of formula (VI) with a compound of formula (VIII), to obtain a compound of formula (VII), optionally in the presence of a suitable acid and a suitable solvent; as shown in the following scheme:

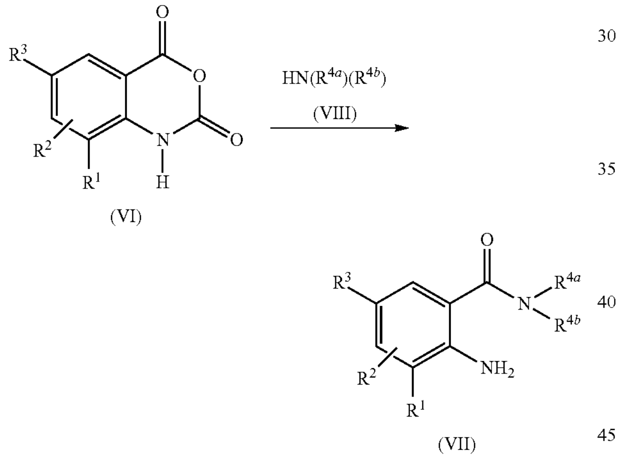

(VI)

(VII)

$R^1$, $R^2$, $R^3$, $R^{4a}$ and $R^{4b}$ have same meaning as define above;

Another aspect of the present invention relates to a process for the preparation of a compound of formula (I) or salts thereof, Formula (I)

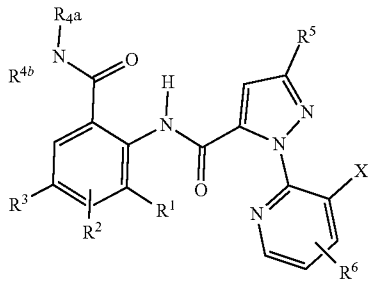

wherein, $R^1$ is selected from the group comprising of halogen, $C_1$-$C_4$ alkyl, $C_1$-$C_4$ haloalkyl and $C_3$-$C_4$-cycloalkyl;

$R^2$ is selected from the group comprising of hydrogen, halogen, cyano, $C_1$-$C_4$ alkyl and $C_3$-$C_4$-cycloalkyl;

$R^3$ is selected from the group comprising of hydrogen, halogen, cyano, $C_1$-$C_4$ haloalkyl or $C_3$-$C_6$ cycloalkyl;

$R^{4a}$ and $R^{4b}$ are independently selected from the group comprising of hydrogen, $C_1$-$C_4$ alkyl, $C_3$-$C_6$ cycloalkyl, $C_3$-$C_6$ cycloalkyl-$C_1$-$C_4$ alkyl; or $NR^{4a}R^{4b}$ represents $-N{=}S(R^7R^8){=}(O)_n$, wherein $R^7$ and $R^8$ are independently selected from the group comprising of $C_1$-$C_4$ alkyl, $C_1$-$C_4$ haloalkyl, $C_3$-$C_6$ cycloalkyl or $C_3$-$C_6$ cycloalkyl $C_1$-$C_4$ alkyl;

n represents an integer from 0-1;

$R^5$ is selected from the group comprising of halogen, $C_1$-$C_4$ alkyl, $C_1$-$C_4$ haloalkyl, $CHF_2$, $CF_3$, $C_1$-$C_4$ alkoxy, $OCHF_2$, $OCH_2CF_3$, or -A-$C_3$-$C_5$ heterocyclyl;

wherein -A- is selected from the group comprising of a direct bond, $CHR^6$, —O— or —S—; and said heterocyclyl may optionally be substituted with one or more group selected from hydrogen, halogen, cyano, $C_1$-$C_4$ alkyl or $C_1$-$C_4$ haloalkyl;

$R^6$ is selected from the group comprising of hydrogen, halogen, cyano, $C_1$-$C_4$ alkyl or $C_1$-$C_4$ haloalkyl;

and

X represents halogen;

comprising the step of reacting a substituted anthranilic amide of formula (VII), (VII)

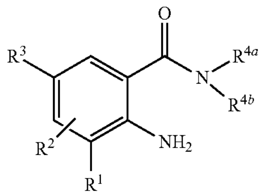

wherein, $R^1$ is selected from the group comprising of halogen, $C_1$-$C_4$ alkyl, $C_1$-$C_4$ haloalkyl and $C_3$-$C_4$-cycloalkyl;

$R^2$ is selected from the group comprising of hydrogen, halogen, cyano, $C_1$-$C_4$ alkyl and $C_3$-$C_4$-cycloalkyl;

$R^3$ is selected from the group comprising of hydrogen, halogen, cyano, $C_1$-$C_4$ haloalkyl or $C_3$-$C_6$ cycloalkyl;

$R^{4a}$ and $R^{4b}$ are independently selected from the group comprising of hydrogen, $C_1$-$C_4$ alkyl, $C_3$-$C_6$ cycloalkyl-$C_1$-$C_4$ alkyl; or $NR^{4a}R^{4b}$ represents $-N{=}S(R^7R^8){=}(O)_n$, wherein $R^7$ and $R^8$ are independently selected from the group comprising of $C_1$-$C_4$ alkyl, $C_1$-$C_4$ haloalkyl $C_3$-$C_6$ cycloalkyl or $C_3$-$C_6$ cycloalkyl $C_1$-$C_4$ alkyl;

n represents an integer from 0-1;

with a pyrazole acid of formula (IX)

(IX)

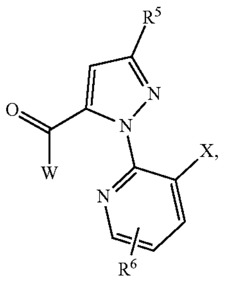

wherein W is OH, Cl, O—$C_1$-$C_4$ alkyl, O—C(O)$C_1$-$C_4$ alkyl or imidazolyl;

$R^5$ is selected from the group comprising of halogen, $C_1$-$C_4$ alkyl, $C_1$-$C_4$ haloalkyl, $CHF_2$, $CF_3$, $C_1$-$C_4$ alkoxy, $OCF_2H$, $OCH_2CF_3$, or -A-$C_3$-$C_5$ heterocyclyl;

wherein -A- is selected from the group comprising of direct bond, $CHR^6$, —O— or —S—; and said heterocyclyl may optionally be substituted with one or more group selected from hydrogen, halogen, cyano, $C_1$-$C_4$ alkyl or $C_1$-$C_4$ haloalkyl;

$R^6$ is selected from the group comprising of hydrogen, halogen, cyano, $C_1$-$C_4$ alkyl or $C_1$-$C_4$ haloalkyl and X represents halogen;

optionally in the presence of a base, a coupling reagent and a suitable solvent, according to the following reaction Scheme as depicted below,

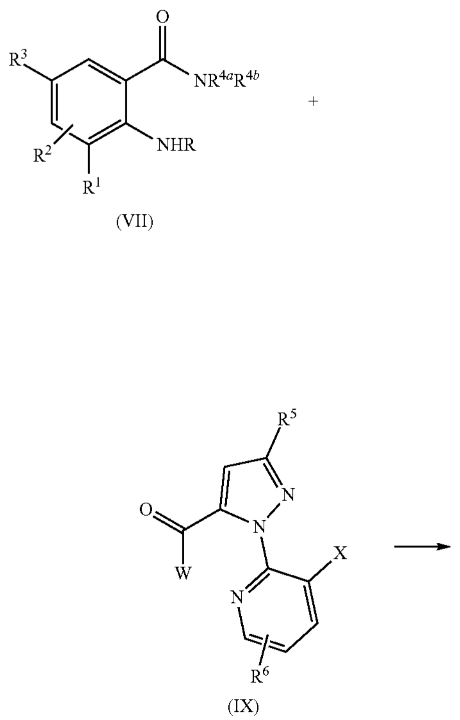

(VII)

(IX)

-continued

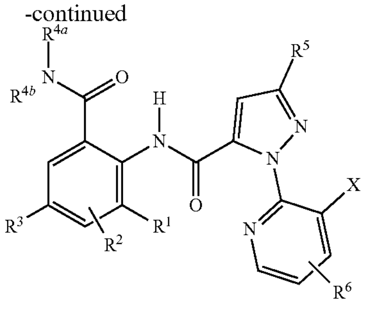

(I)

wherein, the compound of formula (VII)

(VII)

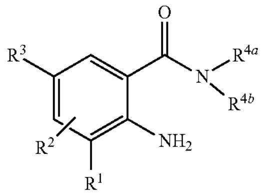

wherein $R^1$ is selected from the group comprising of halogen, $C_1$-$C_4$ alkyl, $C_1$-$C_4$ haloalkyl and $C_3$-$C_4$-cycloalkyl;

$R^2$ is selected from the group comprising of hydrogen, halogen, cyano, $C_1$-$C_4$ alkyl and $C_3$-$C_4$-cycloalkyl;

$R^3$ is selected from the group comprising of hydrogen, halogen, cyano, $C_1$-$C_4$ haloalkyl or $C_3$-$C_6$ cycloalkyl;

$R^{4a}$ and $R^{4b}$ are independently selected from the group comprising of hydrogen, $C_1$-$C_6$ alkyl, $C_3$-$C_6$ cycloalkyl, $C_3$-$C_6$ cycloalkyl-$C_1$-$C_4$ alkyl; or $NR^{4a}R^{4b}$ represent —N═S($R^7R^8$)═$(O)_n$; wherein $R^7$ and $R^8$ are independently selected from the group comprising of $C_1$-$C_4$ alkyl, $C_1$-$C_4$ haloalkyl $C_3$-$C_6$ cycloalkyl or $C_3$-$C_6$ cycloalkyl $C_1$-$C_4$ alkyl and n stands for 0, or 1 is obtained by following the steps comprising of:

a) reacting a compound of formula (II) with a compound of formula (III) to afford a compound of formula (IV), optionally in the presence of a suitable base and a solvent;

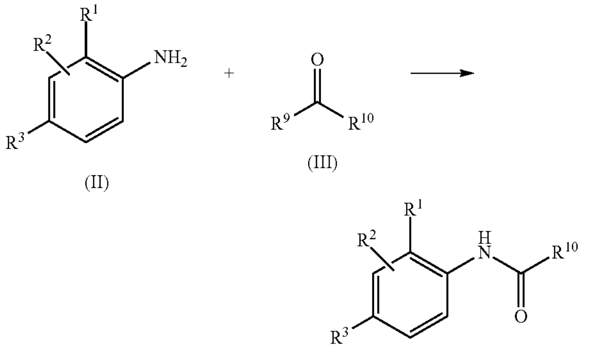

(II)

(III)

(IV)

wherein, $R^1$, $R^2$ and $R^3$ are defined herein above;

$R^9$ is selected from the group comprising of Cl, Br or $C_1$-$C_4$ alkoxy;

$R^{10}$ is selected from the group comprising of cyano, $CH_2X$, $CH_2$—(C═O)—$OR^a$, $CH_2$—(C═O)—$NHR^f$, $COOR^a$, $C(O)R^c$ or $CR^d$═$NR^e$;

$R^a$ is selected from the group comprising of hydrogen or $C_1$-$C_4$-alkyl, $R^c$ is selected from the group comprising of $N(R^a)_2$ or two $R^a$ together with the atoms to which they are attached or together with further atoms selected from the group consisting of C, N, O, S and optionally including 1 to 3 ring members selected from the group consisting of C(═O), C(═), $S(O)_m$ and $SiR'_2$ may form a five to six membered non-aromatic ring;

$R^d$ is selected from the groups comprising of hydrogen and $C_1$-$C_4$-alkyl, (C═O)—$R^a$, $COOR^a$, $CON(R^a)_2$ and phenyl;

$R^e$ is selected from the groups comprising of hydroxy and $C_1$-$C_4$ alkoxy;

$R^f$ is selected from the groups comprising of optionally substituted phenyl, wherein substitution is selected from group comprising of halogen or $C_1$-$C_4$-alkyl;

X represents halogen;

b) reacting the compound of formula (IV) with a suitable acid to obtain an isatin of formula (V), optionally in the presence of a suitable solvent;

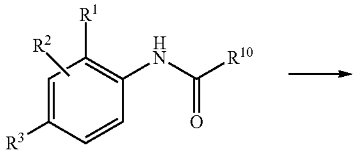

(IV)

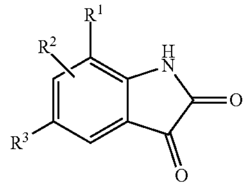

(V)

wherein, $R^1$, $R^2$, $R^3$ and $R^{10}$ have same meaning as define above;

c) oxidizing the isatin of formula (V) to obtain an isatoic anhydride of formula (VI) in the presence of a suitable oxidizing agent and a suitable catalyst, optionally in the presence of a suitable solvent;

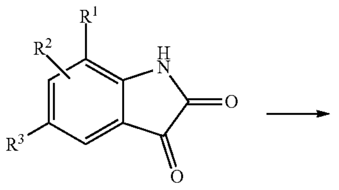

(V)

-continued

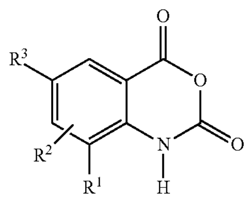

(VI)

wherein, $R^1$, $R^2$, and $R^3$ have the same meaning as defined above;

d) reacting the compound of formula (VI) with a compound of formula (VIII), to obtain a compound of formula (VII), optionally in the presence of a suitable acid and a suitable solvent; as shown in the following scheme:

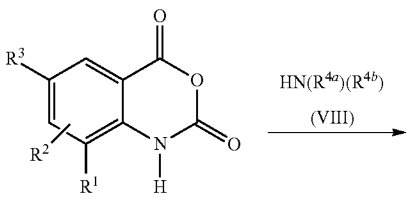

(VI)

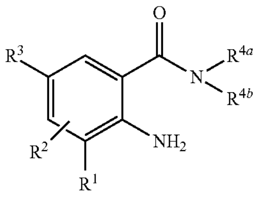

(VII)

wherein $R^1$, $R^2$, $R^3$, $R^{4a}$ and $R^{4b}$ have same meaning as define above;

or the compound of formula (I) is obtained by;

i. reacting the compound of formula (VIIa) with a compound of formula (IX), to obtain a compound of formula (IA),

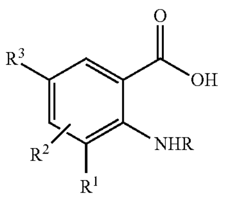

(VIIa)

+

-continued

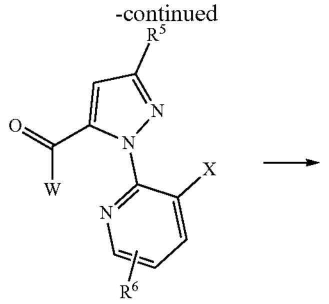

(IX)

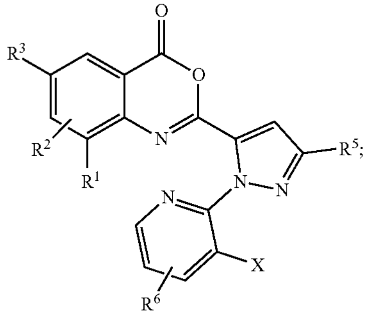

(IA)

ii. reacting the compound of formula (IA) with a substituted amine of formula (VIII) to obtain a compound of formula (I);

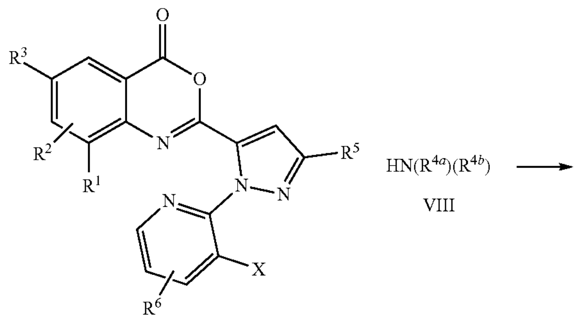

IA

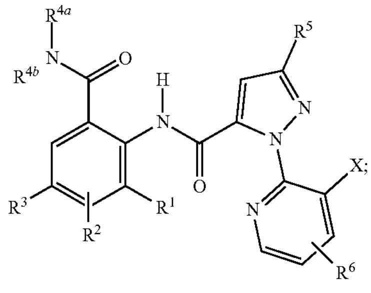

I wherein, compound of formula (VIIa) is obtained by;

hydrolyzing the isatin of formula (V) to obtain an anthranilic acid of formula (VIIa) in the presence of a suitable hydrolysing agent, optionally in the presence of a suitable solvent;

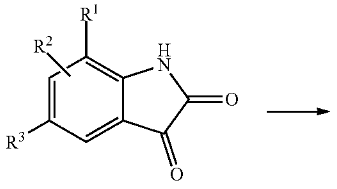

(V)

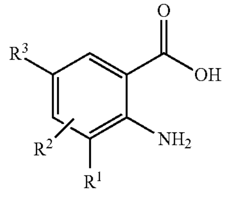

(VIIa)

wherein, $R^1$, $R^2$, and $R^3$ have the same meaning as defined above;

In a second aspect, the present invention relates to a process for the preparation of a compound of formula (VII), (VII)

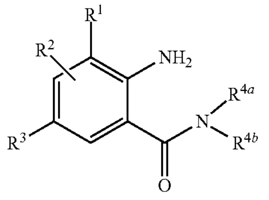

wherein $R^1$, $R^2$, $R^3$, $R^{4a}$ and $R^{4b}$ have the same meaning as define above;

from a compound of formula (IVa), (IVa)

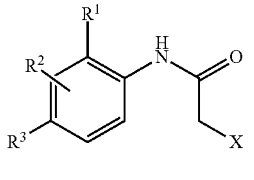

wherein $R^1$, $R^2$, $R^3$ and X have the same meaning as defined above;

In one embodiment, the compound of formula (IVa) is converted to a compound of formula (IVb) by reacting it with a hydroxyl amine derivative in the presence of a suitable base and a suitable solvent, such as for instance isopropanol; as shown in the following Scheme:

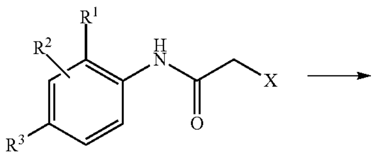

(IVa)

-continued

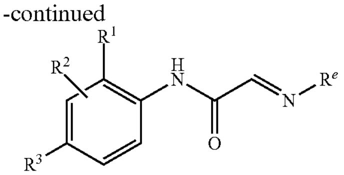

(IVb)

wherein $R^1$, $R^2$, $R^3$, W and X have the same meaning as define above;

further, the compound of formula (IVb) is converted into an isatin of formula (V) by reacting it with a suitable acid such as for instance sulphuric acid in the presence of a suitable solvent such as ethylene dichloride; as shown in following Scheme:

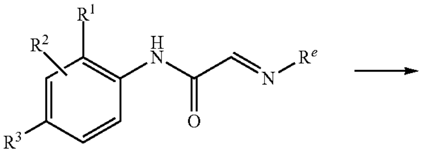

(IVb)

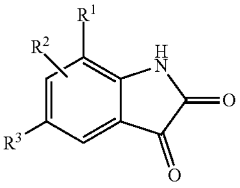

(V)

wherein $R^1$, $R^2$, $R^3$ and $R^e$ have the same meaning as define above;

further, the isatin of formula (V) is oxidised using a suitable oxidizing agent such as hydrogen peroxide or oxone in the presence of an inorganic selenium catalysts such as selenium acid or selenium dioxide to obtain a compound of formula (VI); as shown in the following Scheme:

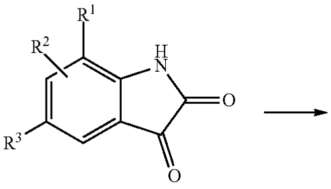

(V)

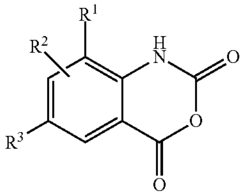

(VI)

wherein $R^1$, $R^2$ and $R^3$ have the same meaning as define above;

The use of a catalyst is necessary for achieving a complete conversion as well as enhancing the reaction rate.

and finally, compounds of formula (VII) are obtained by reacting the compound of formula (VI) with a compound of formula (VIII), to obtain a compound of formula (VII), optionally in the presence of a suitable acid and a suitable solvent; as shown in the following Scheme:

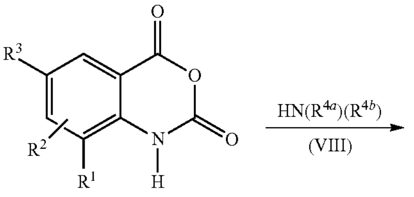

(VI)

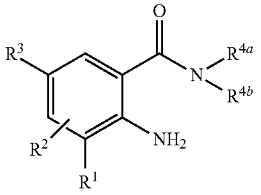

(VII)

wherein $R^1$, $R^2$, $R^3$, $R^{4a}$ and $R^{4b}$ have the same meaning as defined above;

In a third aspect, the present invention relates to a process for the preparation of compounds of formula (V), (V)

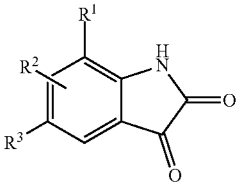

wherein $R^1$, $R^2$ and $R^3$ have same meaning as define above;

from compounds of formula (II), (II)

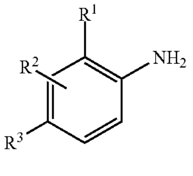

wherein $R^1$, $R^2$ and $R^3$ have the same meaning as defined above;

In one embodiment, the compounds of formula (IVc) are obtained by reacting the compound of formula (II) with a malonate ester of formula $CH_2(COOC_1\text{-}C_2alkyl)_2$ IIIa further the compounds of formula (IVc) may be optionally isolated and can subsequently be converted to compounds of formula (IVd) by reacting them with a nitrite reagent such as sodium nitrite in the presence of a suitable acid such as hydrochloric acid, or with an organic nitrite such as methyl nitrite or ethyl nitrite or another alkyl nitrite in the presence of a suitable solvent; as shown in the following Scheme:

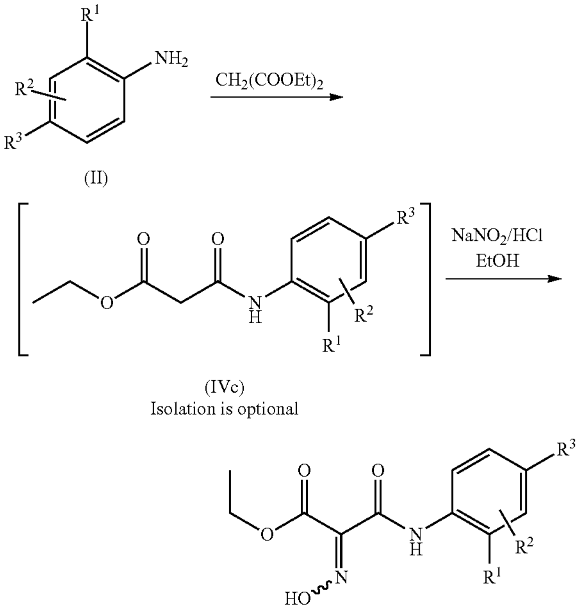

(II)
(IVc)
Isolation is optional
(IVd)

wherein $R^1$, $R^2$ and $R^3$ have same meaning as define above;

further, the compound of formula (IVd) is reacted with a suitable base, preferably sodium hydroxide, in the presence of a suitable solvent such as ethanol to obtain an intermediate of formula (IVe) which can be optionally isolated and further treated with a suitable acid, preferably sulphuric acid, and in the presence of a suitable solvent such as for instance ethylene dichloride to obtain compounds of formula (V); as shown in the following Scheme:

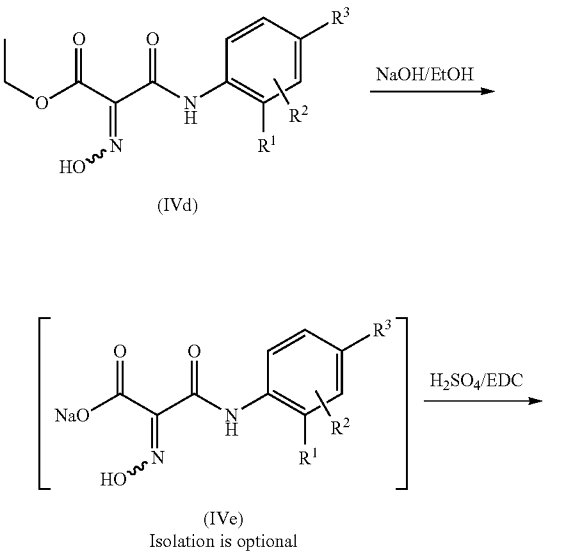

(IVd)
(IVe)
Isolation is optional

-continued

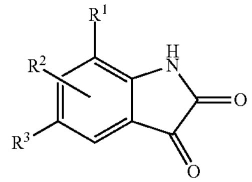
(V)

wherein $R^1$, $R^2$ and $R^3$ have same meaning as define above.

In a fourth aspect, the present invention relates to a process for the preparation of compounds of formula (Vd) and (VIIa), (Vd)

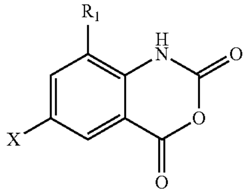

and (VIIa)

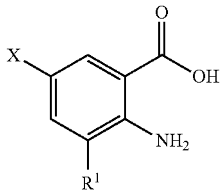

wherein $R^1$ and X have same the meaning as defined above;

from a compound of formula (IV) wherein $R^{10}$ represents $CH_2X$ and $R^3$ represents hydrogen, by this specification representing a compound of formula (IVa-1), (IVa-1)

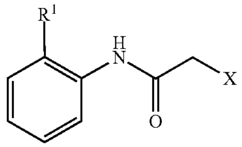

wherein $R^1$ and X have same meaning as defined above.

In one embodiment, the compound of formula (IVa-1) is converted to a compound of formula (Va) by reacting it with a suitable Lewis acid such as for instance aluminium trichloride, optionally in the presence of a suitable solvent; as shown in the following Scheme:

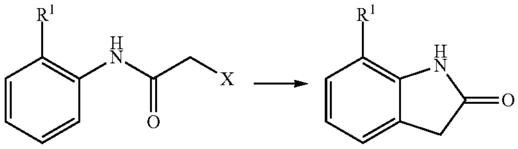
(IVa-1) (Va)

wherein $R^1$ and X have same meaning as define above;

Further, the compound of formula (Va) is converted to a compound of formula (Vb) by reacting it with a halogenating agent such as sulfuryl chloride or chlorine gas or hydrochloric acid/hydrobromic acid with hydrogen peroxide; as shown in the following Scheme:

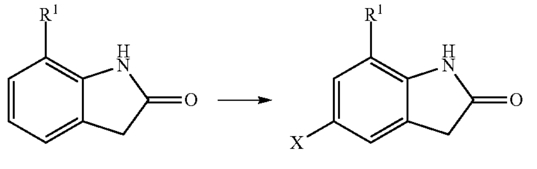

(Va) (Vb)

wherein $R^1$ and X have same meaning as define above.

Further, compounds of formula (Vb) may be optionally converted to a compound of formula (Vc) using a suitable oxidizing agent such as air or oxygen and in the presence of a suitable catalyst such as copper(II) acetate; alternatively the compound of formula (Vb) may be optionally converted to a compound of formula (Vd) by using a suitable oxidizing agent such as for instance hydrogen peroxide, optionally in the presence of a suitable catalyst such as copper(II) acetate; finally reacting the respective compounds of formula (Vc) or (Vd) with a suitable base, at a suitable temperature and in the presence of a suitable solvent to obtain compounds of formula (VIIa); as shown in following Scheme. The compounds of formula (Vc or Vd) may be optionally isolated.

Optionally, a compound of formula (VIIa) is obtained in an one-pot approach from a compound of formula (Vb) in presence of an oxidizing agent, a suitable catalyst such as copper(II) acetate, and subsequent reaction with a suitable base, at a suitable temperature and in presence of a suitable solvent to obtain a compound of formula (VIIa); as shown in the following Scheme:

wherein $R^1$, $R^2$ and $R^3$ have the same meaning as defined above;

from a compound of formula (IV) wherein $R^{10}$ represents $COOR^a$, by this specification representing a compound of formula (IVf), (IVf)

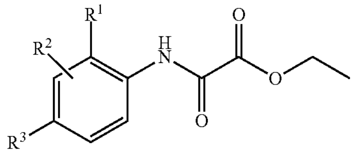

wherein $R^1$, $R^2$ and $R^3$ have the same meaning as defined above.

In one embodiment, a compound of formula (IVf) is converted to a compound of formula (IVg) by reacting it with a suitable amine of formula $NH(R^a)_2$, optionally in the presence of a suitable solvent; as shown in the following Scheme:

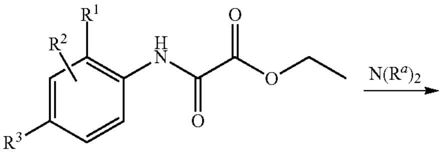

(IVf)

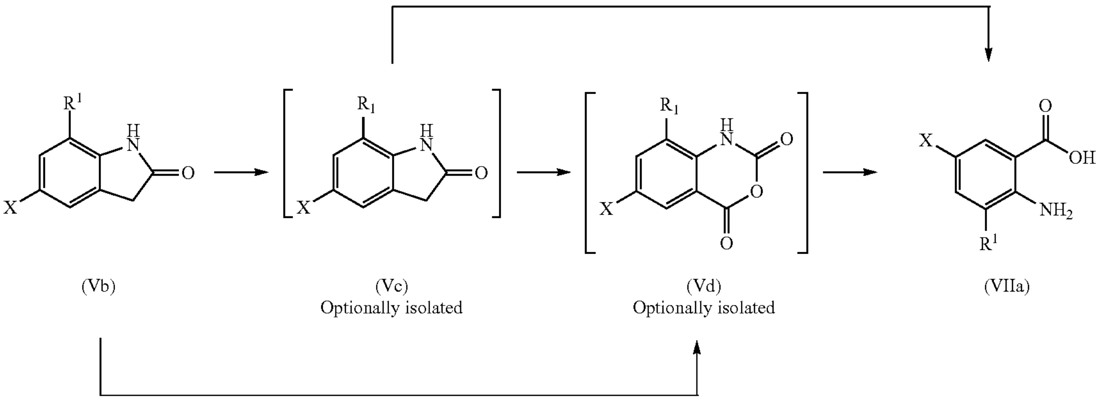

(Vb) (Vc) Optionally isolated (Vd) Optionally isolated (VIIa)

wherein $R^1$, $R^2$, $R^3$ and X have same meaning as defined above.

In a fifth aspect, the present invention relates to a process for the preparation of a compound of formula (V), (V)

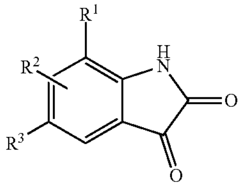

-continued

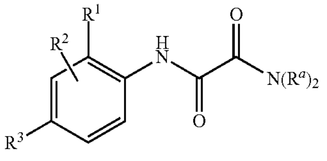

(IVg)

wherein $R^1$, $R^2$, $R^3$ and $R^c$ have same meaning as define above;

Further, the compound of formula (IVg) is converted to a compound of formula (V) by reacting with a suitable reagent-2 such as phosphorous oxychloride or polyphosphoric acid at a suitable temperature; as shown in the following Scheme:

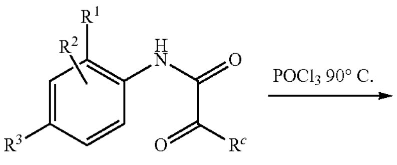

(IVg)

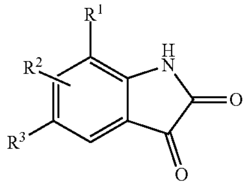

(V)

wherein $R^1$, $R^2$ and $R^3$ have same meaning as define above;

In another embodiment, a compound of formula (IVf) is converted to the compound of formula (IVh) by reacting with ammonia, optionally in the presence a suitable solvent; as shown in following

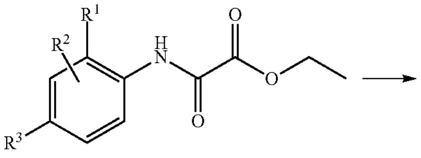

(IVf)

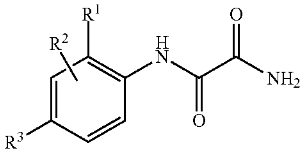

(IVh)

wherein $R^1$, $R^2$ and $R^3$ have the same meaning as defined above;

Further, a compound of formula (IVh) is converted to a compound of formula (IVi) by reacting it with a suitable reagent-2 such as phosphorous oxychloride; as shown in the following Scheme:

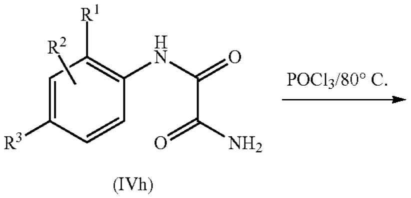

(IVh)

-continued

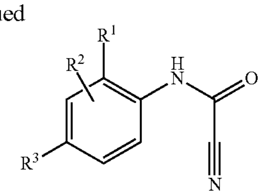

(IVi)

wherein $R^1$, $R^2$ and $R^3$ have the same meaning as defined above;

Further, compounds of formula (IVi) can be converted to compounds of formula (V) by reacting them with a Lewis acid at a suitable temperature and optionally in the presence of a suitable solvent; as shown in the following Scheme:

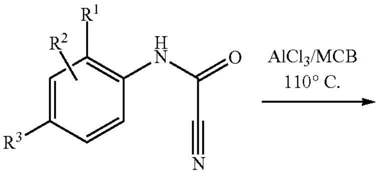

(IVi)

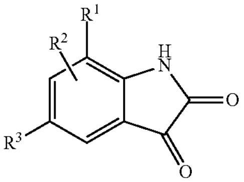

(V)

wherein $R^1$, $R^2$ and $R^3$ have the same meaning as defined above.

In a sixth aspect, the present invention relates to a process for the preparation of a compound of formula (V), (V)

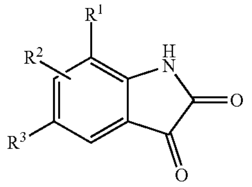

wherein $R^1$, $R^2$ and $R^3$ have the same meaning as defined above;

from a compound of formula (II), (II)

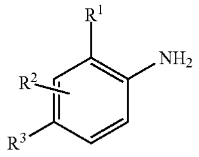

wherein $R^1$, $R^2$ and $R^3$ have the same meaning as defined above;

In one embodiment, a compound of formula (IV) wherein $R^{10}$ represents $CR^d{=}NR^e$, by this specification representing a compound of formula (IVj), can be prepared by reacting a compound of formula (II) with a compound of formula (X) or (XI), optionally in the presence of a solvent. Subsequently, compounds of formula (IVj) can be converted to compounds of formula (V) in the presence of a suitable acid such as sulphuric acid and a suitable solvent such as ethylene dichloride to obtain compounds of formula (V); as shown in the following Scheme:

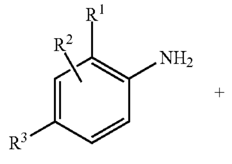

(II)

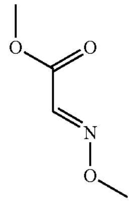

or

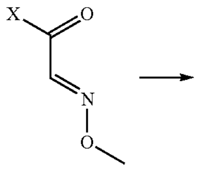

(X) (XI)

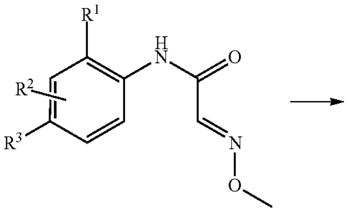

(IVj)

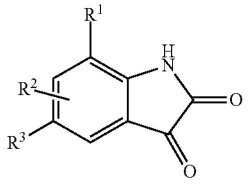

(V)

wherein $R^1$, $R^2$ and $R^3$ have the same meaning as defined above.

In a seventh aspect, the present invention relates to a process for the preparation of halogenated intermediates such as compounds of formula (V) or (IV), wherein $R^3$ represents halogen.

In one embodiment, compounds of formula (V) wherein $R^3$ represents hydrogen, by this specification representing compounds of formula (Vd), can be converted to compounds of formula (Ve) by reacting them with an appropriate halogenating agent such as for instance chlorine gas; as shown in the following Scheme:

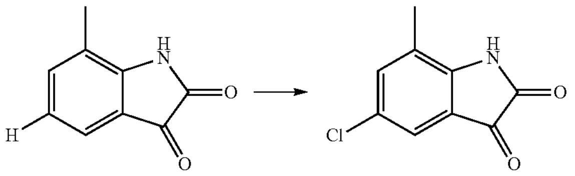

(Vd) (Ve)

In another embodiment, compounds of formula (IV) wherein $R^3$ represents hydrogen, by this specification representing compounds of formula (IVa-1), can be converted to compounds of formula (IVa-2) by reacting them with halogenating agents such as for instance chlorine gas or hydrochloric acid/hydrobromic acid and hydrogen peroxide; as shown in the following Scheme:

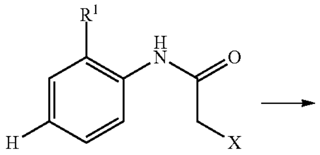

(IVa-1)

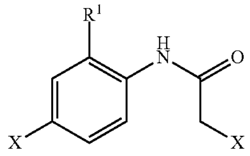

(IVa-2)

wherein $R^1$ and X have the same meaning as defined above;

The compounds of formula (IX) can be obtained by either of the processes disclosed in WO2003015518, WO20030155519, WO2011157664 and WO2013030100.

The cyanation of the isatin of formula (V) or of the isatoic anhydride of formula (VI) or of the compounds of formula (VII) can be carried out according to processes reported in WO2008010897, WO2008070158, WO2009085816, WO2009061991, WO2009006061 and WO2008082502.

The halogenations as described in the present invention are carried out in the presence of suitable halogenating reagents which include, but are not limited to, HX, NaX, KX, $CuX_2$, $MgX_2$, CsX, $ZnX_2$, $SOCl_2SO_2Cl_2$, $COCl_2$, $X_2$, $C({=}O)(OCl_3)_2$, t-BuOCl, NaOCl, Chloramine-T, N-halosuccinamides, methane sulfonyl chloride, $POX_3$, $PX_3$, $PX_5$ or metal halides; wherein X is Cl, Br, I or F.

The suitable oxidizing agents as described in the present invention include, but are not limited to, hydrogen peroxide, oxone, hydrogen peroxide, t-butyl-hydroperoxide, tungstic peroxide, m-chloroperbenzoic acid, benzoyl peroxide, hypohalgenous acids, ceric ammonium nitrate, hypoceric ammonium nitrate, oxone, periodic acid, peracetic acid, performic acid hydrogen peroxide urea-adduct, sodium perborate, pyridinium chlorochromate, pyridinium dichromate, ruthenium(II) oxide, manganese(II) oxide, copper(II) acetate/$O_2$, dimethyl sulfoxide and the like. Preferably the suitable oxidizing agent is hydrogen peroxide.

The halogenating reagents useful for converting the diones of formula (Va) into the compounds of formula (Vb) are selected, but are not limited to, from HX, $CuX_2$, $MgX_2$, CsX, $ZnX_2$, $SOCl_2$, $SO_2Cl_2$, $COCl_2$, $X_2$, $C(=O)(OCl_3)_2$, t-BuOCl, NaOCl, Chloramine-T, N-halosuccinimides, methane sulfonyl chloride, $POX_3$, $PX_3$, $PX_5$ or metal halides; wherein X is Cl, Br, I or F.

The oxidizing agents useful for converting the diones of formula (V) into the isatoic anhydrides of formula (VI) are selected, but are not limited to, from hydrogen peroxide, t-butyl-hydroperoxide, tungstic peroxide, m-chloroperbenzoic acid, benzoyl peroxide, hypohalogenous acids, ceric ammonium nitrate, oxone, periodic acid, peracetic acid, performic acid hydrogen peroxide urea-adduct, sodium perborate, pyridinium chlorochromate, pyridinium dichromate, ruthenium(II) oxide, manganese(II) oxide, copper(II) acetate/$O_2$ and dimethyl sulfoxide.

The suitable catalyst used for the above mentioned oxidation is selected from selenic acid, selenous acid, selenium dioxide, copper(II) acetate, tungstic acid, $(PhSe)_2$, boric acid, acetic acid, $H_2SO_4$, conc. aq. HCl. Preferably the suitable catalyst is selected from selenium compounds, as for example selenic acid, selenous acid or selenium dioxide, or acetic acid The suitable acid used in the present invention is selected from hydrochloric acid, hydrobromic acid, sulfuric acid, formic acid, acetic acid, trifluoroacetic acid, propionic acid, methanesulfonic acid, benzenesulfonic acid, p-toluenesulfonic acid, an acidic ion-exchange resin or mixture thereof.

The suitable acid used for conversion of substituted isatoic anhydrides of formula (VI) to substituted anthranilic amides of formula (VII) is selected from weak acids such as acetic acid, p toluenesulfonic acid (pTSA) and the like.

The most suitable acid for converting compounds of formula (IV) into isatins of formula (V) is sulphuric acid.

The solvents useful in carrying out the reaction steps mentioned in the present invention are selected from aliphatic hydrocarbons such as hexane, heptane, octane, nonane, decane, dodecane, decaline and the like; alicyclic hydrocarbons such as cycloalkanes: cyclobutane, cyclopentane, cyclohexane, cycloheptane, cyclooctane, and the like; aromatic hydrocarbons such as toluene, xylene, mesitylene, benzene and the like; halogenated aromatic hydrocarbons as chlorobenzene, 1,2-dichlorobenzene, 1,3-dichlorobenzene and the like; ethers such as diisopropyl ether, t-butyl methyl ether, tetrahydrofuran, 2-methyl tetrahydrofuran, dioxane, monoglyme, diglyme, methoxy-methane, methoxy-ethane, ethoxy-ethane, di-methoxyethane, di-ethoxyethane and the like; alcohols such as methanol, ethanol, n- or i-propanol, n-, i-, sec- or tert-butanol, ethanediol, propane-1,2-diol, ethoxyethanol, methoxyethanol, ketones such as acetone, ethyl methyl ketone. esters such as ethyl acetate and methyl acetate; halogenated hydrocarbons such as dichloromethane, chloroform, dichloroethane and the like; nitriles, such as acetonitrile, propionitrile; polar aprotic solvents such as N,N-dimethyformamide, dimethyl sulfoxide, N-methyl-2-pyrrolidone, 1,3-dimethyl-3,4,5,6-tetrahydro-2(1H)-pyrimidinone, hexamethylphosphortriamide, 1,3-dimethyl-2-imidazolidinone and the like; water or mixtures thereof.

The solvent useful in carrying out the acylation reaction mentioned in the present invention is selected from aliphatic hydrocarbons such as hexane, heptane, octane, nonane, decane, dodecane and the like; alicyclic hydrocarbons such as cycloalkanes: cyclobutane, cyclopentane, cyclohexane, cycloheptane, cyclooctane, and the like; aromatic hydrocarbons such as toluene, xylene, mesitylene, benzene and the like; halogenated aromatic hydrocarbons as chlorobenzene, 1,2-dichlorobenzene, 1,3-dichlorobenzene and the like; ethers such as diisopropyl ether, t-butyl methyl ether, tetrahydrofuran, 2-methyl tetrahydrofuran, halogenated hydrocarbons such as dichloromethane, chloroform, dichloroethane and the like; polar aprotic solvents such as N,N-dimethylformamide, dimethyl sulfoxide, N-methyl-2-pyrrolidone. Preferably halogenated hydrocarbons such as dichloromethane, dichloroethane and the like; aromatic hydrocarbons such as toluene and xylene.

The solvent useful in carrying out the oxime formation reaction mentioned in the present invention is selected from alcohols such as methanol, ethanol, n- or i-propanol, n-, i-, sec- or tert-butanol, ethanediol, propane-1,2-diol, ethoxyethanol, methoxyethanol, polar aprotic solvents such as N,N-dimethylformamide, dimethyl sulfoxide, N-methyl-2-pyrrolidone. Preferably alcohols such as ethanol, n- or i-propanol, n-, i-, sec- or tert-butanol and ethanediol are perceived as useful.

The solvents useful in carrying out the reaction step b mentioned in the present invention are selected from halogenated hydrocarbons such as dichloromethane, chloroform, dichloroethane and the like.

The solvents useful in carrying out the reaction step c mentioned in the present invention are selected from aliphatic hydrocarbons such as hexane, heptane, octane, nonane, decane, dodecane, decaline and the like; alicyclic hydrocarbons such as cycloalkanes: cyclobutane, cyclopentane, cyclohexane, cycloheptane, cyclooctane, and the like; aromatic hydrocarbons such as toluene, xylene, mesitylene, benzene and the like; halogenated aromatic hydrocarbons as chlorobenzene, 1,2-dichlorobenzene, 1,3-dichlorobenzene and the like; ethers such as diisopropyl ether, t-butyl methyl ether, tetrahydrofuran, 2-methyl tetrahydrofuran, halogenated hydrocarbons such as dichloromethane, chloroform, dichloroethane and the like; polar aprotic solvents such as N,N-dimethylmethanamide, dimethyl sulfoxide, N-methyl-2-pyrrolidone. Preferred are halogenated hydrocarbons such as dichloromethane, chloroform, dichloroethane and the like.

The solvents useful in carrying out the reaction step d mentioned in the present invention are selected from ethers such as diisopropyl ether, t-butyl methyl ether, tetrahydrofuran, 2-methyl tetrahydrofuran, dioxane, monoglyme, diglyme, methoxy-methane, methoxy-ethane, ethoxy-ethane, di-methoxyethane, di-ethoxyethane and the like; esters such as ethyl acetate and methyl acetate.

The reaction steps mentioned in the present invention can also be carried out in the absence of solvents.

The oximes of formula (IVb) and (IVd) are converted to the compounds of formula (V) by using mineral acids selected from, but not limited to, sulfuric acid, hydrochloric acid and nitric acid, usually under stirring or other means of mixing within a temperature ranging from 0° C. to 150° C.

The obtained diones of formula (V) are converted into isatoic anhydrides of formula (VI) using a suitable halogenating reagent, one or more suitable oxidizing agent/s and one or more suitable solvents at a temperature ranging from 0° C. to 250° C., preferably 25° C. to 150° C.

In a preferred embodiment, the suitable coupling reagent is selected from 1-(3-dimethylaminopropyl)-3-ethylcarbodiimide hydrochloride (EDC), dicyclohexylcarbodiimide (DCC), 1-cyclohexyl-3-(2-morpholmoethyl)carbodiimide, 1,3-di-tert-butylcarbodiimide, 1-(dimethylaminopropyl)-3-ethylcarbodiimide methiodide, 1-tert-butyl-3-(liphenylmethyl)-carbodiimide, 1,3-diisopropylcarbodiimide, bis-(diphenylmethyl)-carbodiimide, 1-tert-butyl-3-ethylcarbodiimide, 1-methyl-2-chloropyridinium iodide, 2-ethoxy-1-ethoxycarbonyl-1,2-dihydroquinoline (EEDQ), BOP-chloride and isobutyl chloroformate.

The compounds of formula (I) are obtained from the compounds of formula (VII) and compounds of formula (IX) wherein W is OH using a suitable reagent such as $SOCl_2$, $SO_2Cl_2$, $COCl_2$, $X_2$, $C(=O)(OCl_3)_2$, chloramine-T, methane sulfonyl chloride, $POX_3$, $PX_3$, $PX_5$ or metal halides; wherein X is Cl, Br.

The compound of formula (I) is obtained from the compound of formula (VII) and a compound of formula (IX) wherein W is Cl, O—$C_1$-$C_4$ alkyl using suitable reagents such as triethylamine, diisopropylamine, diisopropyl ethyl amine, pyridine, alkylated and dialkylated pyridines, dimethylamino pyridine, and the like, or of mixtures thereof.

The compounds of formula (IVg) are converted into the compounds of formula (V) by reacting them with suitable reagents-2 such as phosphorous oxychloride, $PX_3$, or polyphosphoric acid.

Inorganic bases are preferably selected in a not limiting way from the group comprising of alkali or alkaline earth metal hydroxide, carbonate, bicarbonate and the like, wherein the alkali and alkaline earth metals are selected from the group comprising of lithium, sodium, potassium, rubidium, caesium, calcium, magnesium, barium and the like or of mixtures thereof.

The organic bases are preferably selected in a not limiting way from the group comprising of amines as methylamine, dimethyl amine, diethyl amine, triethylamine, diisopropylamine, diisopropyl ethyl amine, pyridine, alkylated and dialkylated pyridines, dimethylamino pyridine, piperidine, and the like or of mixtures thereof.

Suitable Lewis acids being useful for converting substituted anilines of formula (IVa-1) or (IVi) into compounds of formula (Va) or (V) are selected in a not limiting way from to $AlX_3$, $BX_3$, $FeX_3$, $ZnX_2$, $GaX_3$, $InX_3$, $TiX_4$, $BiX_3$, $SbX_3$, $SnX_2$, $SnX_4$, $SiX_4$, hypovalent Lewis acids and the like, wherein X stands for f, Cl and Br.

Suitable hydrolyzing agentas for the conversion of the isatins of formula (V) into anthranilic acids of formula (VIIa) are acids or inorganic bases, optionally in the presence of oxidizing agents; the respective acids are selected in a non-limiting way from sulfuric acid, hydrochloric acid, acetic acid, trifluoroacetic acid; the inorganic bases are selected in a non-limiting way from alkali or alkaline earth metal hydroxides, and the like, for examples from sodium hydroxide, potassium hydroxide and the like or of mixtures thereof. Furthermore, the oxidising agent is preferably hydrogen peroxide.

The preferred suitable hydrolyzing agent for the conversion of the isatins of formula (V) to anthranilic acids of formula (VIIa) is sulfuric acid.

An embodiment of the present invention provides the compound of formula (VII), wherein, $R^{4a}$ and $R^{4b}$ are independently selected from hydrogen, methyl, ethyl, isopropyl, t-butyl, methyl cyclopropyl or ethyl cyclopropyl.

In a preferred embodiment, the present invention provides the process for synthesis of a compound of formula (VII), Formula (VII)

(VII)

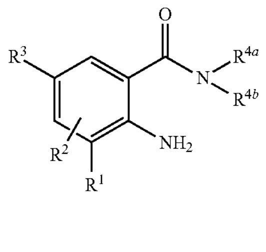

wherein, $R^1$ is methyl or halogen; more preferably $R^1$ is methyl, chloro or bromo;

$R^2$ is hydrogen or halogen; more preferably $R^2$ is hydrogen or fluoro;

$R^3$ is halogen or cyano; more preferably $R^3$ is chloro, bromo or cyano;

$R^{10}$ is $CX_3$, $OR^9$ or $NR^{4a}R^{4b}$;

$R^{4a}$ is methyl, ethyl, n-propyl, iso-propyl, cyclopropyl methylcyclopropyl, ethylcyclopropyl, iso-butyl, tert-butyl; $R^{4b}$ is hydrogen or methyl, X is halogen; more pereferably chloro or bromo;

$R^9$ hydrogen, methyl, ethyl n-propyl, iso-propyl, iso-butyl, tert-butyl.

In another preferred embodiment, the present invention provides the process for synthesis of a compound of formula (I), Formula (I)

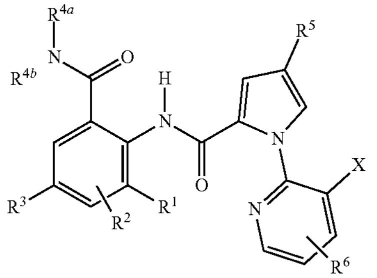

wherein, $R^1$ is methyl or halogen; more preferably $R^1$ is methyl, chloro or bromo;

$R^2$ is hydrogen or halogen; more preferably $R^2$ is hydrogen or fluoro;

$R^3$ is halogen or cyano; more preferably $R^3$ is chloro, bromo or cyano;

$R^{4a}$ is methyl, ethyl, n-propyl, iso-propyl, cyclopropyl methylcyclopropyl, ethylcyclopropyl, iso-butyl, tert-butyl; $R^{4b}$ is hydrogen or methyl, X is halogen; more pereferably fluoro, chloro or bromo;

$R^5$ is bromo, chloro, $CF_3$, or -A-$C_3$-$C_5$ heterocyclyl;

wherein -A- is selected from the group comprising of direct bond, $CHR^6$, —O— or —S—; and said heterocyclyl may optionally be substituted with one or more group selected from hydrogen, halogen, cyano, $C_1$-$C_4$ alkyl or $C_1$-$C_4$ haloalkyl;

$R^6$ is selected from the group comprising of hydrogen, halogen, cyano, $C_1$-$C_4$ alkyl or $C_1$-$C_4$ haloalkyl.

In one embodiment, the present invention provides a process for the synthesis of a compound of formula (I) wherein $R^5$ is bromo or optionally substituted 3-5 membered heterocycle.

In preferred embodiment, the present invention provides a process for the synthesis of a compound of formula (I) wherein $R^5$ is bromo or optionally substituted 4-5 membered heterocycle.

In more preferred embodiment, the present invention provides a process for the synthesis of a compound of formula (I) wherein $R^5$ is bromo or optionally substituted 5 membered heterocycle.

In one more preferred embodiment, the present invention provides a process for the synthesis of a compound of formula (I) wherein $R^5$ is bromo or

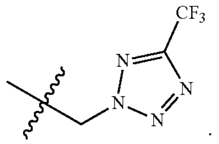 [SMILES: *Cn1nnc(C(F)(F)F)n1]

In one embodiment the compound of formula (I) comprises of chlorantraniliprole, cyantraniliprole, cyclaniliprole, tetraniliprole, tetra-chlorantraniliprole, bromantraniliprole or fluchlordiniliprole.

Any person skilled in the art knows the best work-up of the reaction mixtures after the end of the respective reactions. In one embodiment, the work-up is usually carried out by isolation of the product by filtration, and optionally washing with solvent, further optionally drying of the product if required.

The process steps according to the invention are generally carried out under atmospheric pressure. Alternatively, however, it is also possible to work under increased or reduced pressure.

Without further elaboration, it is reasonable to believe that any person skilled in the art who is using the preceding description can utilize the present invention to its fullest extent. The following examples are therefore to be interpreted as merely illustrative and not limiting of the disclosure in any way whatever.

EXAMPLES

Example-1: Synthesis of 2-chloro-N-(4-chloro-2-methylphenyl)acetamide

Process-1

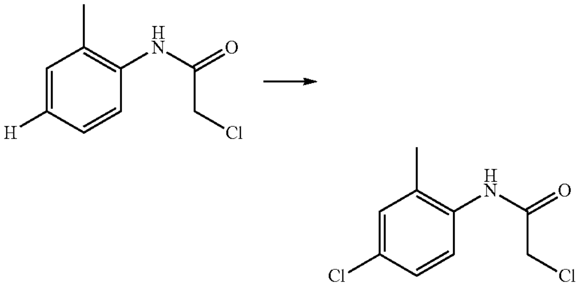

To a solution of 2-chloro-N-(o-tolyl)acetamide (2 g, 10.5 mmol) in acetic acid (16 mL), 37% hydrochloric acid (1.17 mL, 11.55 mmol) was added followed by slow addition of 30% aqueous hydrogen peroxide (1.45 mL, 23.10 mmol) at 15° C. The reaction mixture was stirred at 25-30° C. for 15 h. After completion of the reaction, water (4 mL) was added to the reaction mixture. The resulting precipitated product was filtered and dried under reduced pressure to obtain 2-chloro-N-(4-chloro-2-methylphenyl)acetamide (1.89 g, 8.19 mmol).

$^1$H-NMR (DMSO-$d_6$, 400 MHz): 9.68 (s, 1H), 7.42 (d, J=8.4 Hz, 1H), 7.31 (d, J=2.4 Hz, 1H), 7.23 (dd, J1=2.4 Hz, J2=2.8 Hz, 1H), 4.29 (s, 2H), 2.19 (s, 3H); MS: m/z=217 [M−H]

Process-2

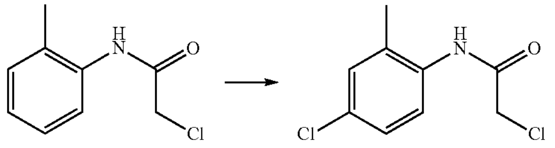

To a solution of 2-chloro-N-(o-tolyl)acetamide (50 g, 272 mmol) in DCE (350 mL), a solution of sulfuryl chloride (42.4 g, 299 mmol) in dichlorethane (DCE) (50 mL) was added at 0° C. during 2 h. The reaction mixture was stirred at 25° C. for 12 h. After completion of the reaction, excess solvent was distilled off under reduced pressure, and water (200 mL) was added. The resulting precipitated product was filtered, washed with water (50 mL) and dried under reduced pressure to obtain 2-chloro-N-(4-chloro-2-methylphenyl)acetamide (45.6 g, 210 mmol).

Example-2: Synthesis of N-(4-bromo-2-methylphenyl)-2-chloroacetamide

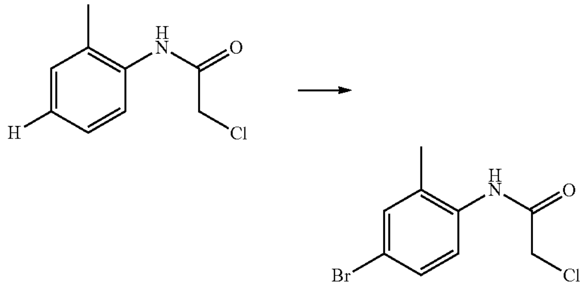

To a solution of 2-chloro-N-(o-tolyl)acetamide (1 g, 5.45 mmol) in acetic acid (5 mL), 30% aqueous hydrogen peroxide (2.22 mL, 32.7 mmol) was added, followed by slow addition of 48% aqueous hydrobromic acid (0.93 g, 5.45 mmol) at 15° C. The reaction mixture was stirred at 25-30° C. for 15 h. After completion of the reaction, water (4 mL) was added to the reaction mixture. The resulting precipitated product was filtered and dried under reduced pressure to obtain N-(4-bromo-2-methylphenyl)-2-chloroacetamide (1.07 g, 4.08 mmol).

$^1$H-NMR (DMSO-$d_6$, 400 MHz): 9.69 (s, 1H), 7.44 (d, J=2.0 Hz, 1H), 7.37 (s, 1H), 7.36 (d, J=2.0 Hz, 1H), 4.30 (s, 2H), 2.19 (s, 3H); MS: m/z=261.8 [M−H]

Example-3: Synthesis of N-(4-chloro-2-methylphenyl)-2-(hydroxyimino)acetamide

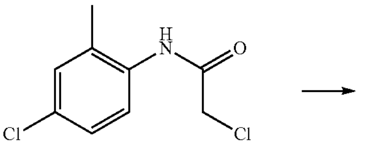

-continued

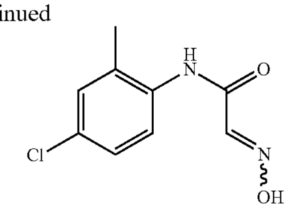

To a suspension of 2-chloro-N-(4-chloro-2-methylphenyl) acetamide (24 g, 110 mmol) in 2-propanol (212 mL), hydroxyl amine hydrochloride (22.9 g, 330 mmol) was added, followed by slow addition of N,N diisopropylethylamine (DIPEA) (43.7 g, 330 mmol) at 25-30° C. The resulting suspension was stirred for 18 h at 78° C. After completion of the reaction, the solvent (2-propanol) was evaporated, and to the obtained residue water (100 mL) was added. The resulting precipitated product was filtered and dried under reduced pressure to obtain N-(4-chloro-2-methylphenyl)-2-(hydroxyimino)acetamide (17.34 g, 81.4 mmol).

$^1$H-NMR (DMSO-$d_6$, 400 MHz): 12.2 (br, 1H), 9.56 (s, 1H), 7.68 (s, 1H), 7.50 (d, J=8.8 Hz, 1H), 7.36 (dd, J1=8.4, J2=2.4 Hz, 1H), 7.31 (d, J=2.4 Hz, 1H), 2.19 (s, 3H); MS: m/z=211 [M−H]

Example-4: Synthesis of N-(4-bromo-2-methylphenyl)-2-(hydroxyimino)acetamide

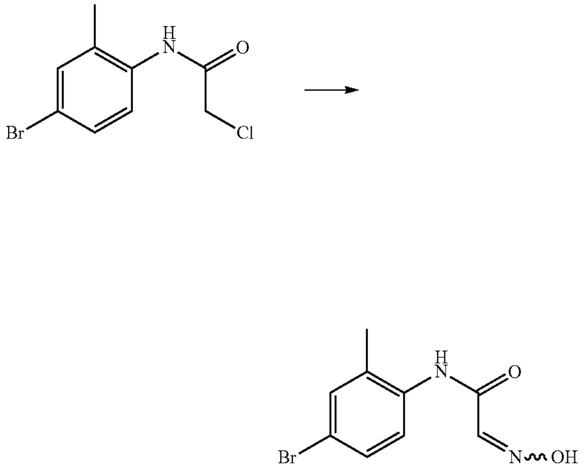

To a suspension of N-(4-bromo-2-methylphenyl)-2-chloroacetamide (3 g, 11.4 mmol) in 2-propanol (25 mL), hydroxyl amine hydrochloride (2.4 g, 34.2 mmol) was added, followed by slow addition of N,N diisopropylethylamine (DIPEA) (4.4 g, 34.2 mmol) at 25-30° C. The resulting suspension was stirred for 18 h at 78° C. After completion of the reaction, the solvent (2-propanol) was distilled off, and water (12 mL) was added to the residue. The resulting precipitated product was filtered and dried under reduced pressure to obtain N-(4-bromo-2-methylphenyl)-2-(hydroxyimino)acetamide (2.3 g, 9.12 mmol).

$^1$H-NMR (DMSO-$d_6$, 400 MHz): 12.22 (s, 1H), 9.52 (s, 1H), 7.67 (s, 1H), 7.46-7.45 (m, 1H), 7.44 (s, 1H), 7.35 (dd, J1=8.4, J2=2.4 Hz, 1H), 2.19 (s, 3H); MS: m/z=256 [M−H]

Example-6: In-Situ-Synthesis of 2-chloro-N-(4-chloro-2-methylphenyl)acetamide from o-toluidine

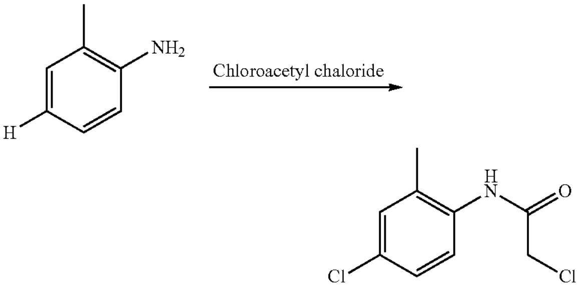

To a solution of o-toluidine (590 g, 4573 mmol) in dichlorethane (DCE) (2400 mL), triethyl amine (532 mL, 5259 mmol) was added at 25° C. The mixture was cooled to 0° C. and a solution of 2-chloroacetyl chloride (614 mL, 5259 mmol) in dichlorethane (DCE)(400 mL) was slowly added at 0-10° C. The reaction mixture was stirred for 4 h at 25-30° C. After complete consumption of o-toluidine, the reaction mixture was cooled to 0° C. and a solution of sulfuryl chloride (715 g, 5030 mmol) in DCE (400 mL) was added during 4 h and stirred at 25° C. for 12 h. After completion of the reaction, excess solvent was distilled at reduced pressure and water (2000 mL) was added to it. The resulting precipitated product was filtered, washed with water (500 mL×2) and dried under reduced pressure to obtain 2-chloro-N-(4-chloro-2-methylphenyl)acetamide (842 g, 3864 mmol).

Example-6: Synthesis of N-(2-bromo-4-chlorophenyl)-2-(hydroxyimino)acetamide

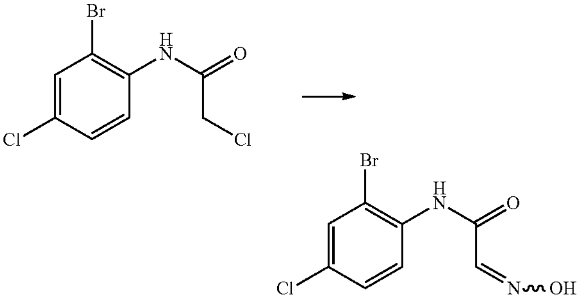

To a suspension of N-(2-bromo-4-chlorophenyl)-2-chloroacetamide (3 g, 10.6 mmol) in 2-propanol (25 mL), hydroxyl amine hydrochloride (2.2 g, 31.8 mmol) was added, followed by slow addition of N,N-diisopropylethylamine (DIPEA) (4.1 g, 31.8 mmol) at 25-30° C. The resulting suspension was stirred for 18 h at 78° C. After completion of the reaction, the solvent (2-propanol) was distilled off and water (12 mL) was added to the residue. The resulting precipitated product was filtered and dried under reduced pressure to obtain N-(2-bromo-4-chlorophenyl)-2-(hydroxyimino)acetamide (2.1 g, 7.4 mmol).

$^1$H-NMR (DMSO-$d_6$, 400 MHz): 12.45 (br, 1H), 9.48 (s, 1H), 7.90 (d, J=8.4, 1H), 7.81 (s, 1H), 7.65 (s, 1H), 7.42 (d, J=4, 1H); MS: m/z=276.8 [M−H]

Example-7: Synthesis of 5-chloro-7-methylindoline-2,3-dione

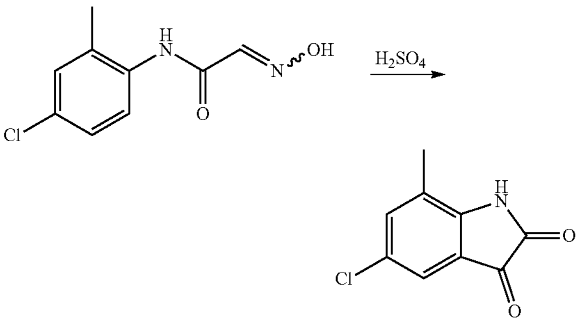

To a stirred mixture of ethylene dichloride (100 g) and sulphuric acid (81 g, 826 mmol), N-(4-chloro-2-methylphenyl)-2-(hydroxyimino)acetamide (25 g, 118 mmol) was added portion-wise at 0-10° C. The reaction mixture was stirred at 20-25° C. for 16 h. After completion of the reaction, the reaction mixture was quenched by addition of ice cold water (250 g). The reaction mass was further heated to 45-50° C. under stirring for 1 h. The precipitate obtained was filtered and dried under reduced pressure to obtain 5-chloro-7-methylindoline-2,3-dione (20.7 g, 106 mmol $^1$H-NMR (400 MHz, DMSO-$d_6$) δ 11.18 (s, 1H), 7.48 (d, J=2 Hz, 1H), 7.35 (d, J=2 Hz, 1H), 2.16 (s, 3H). MS: m/z=194 [M−H]

Example-8: Synthesis of 5-bromo-7-methylindoline-2,3-dione

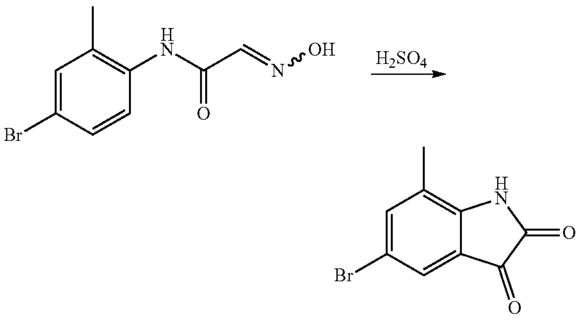

To a stirred mixture of ethylene dichloride (12 g) and sulphuric acid (8.2 g, 84 mmol), N-(4-bromo-2-methylphenyl)-2-(hydroxyimino)acetamide (3 g, 12 mmol) was added portion-wise at 0-10° C. The reaction mixture was stirred at 20-25° C. for 16 h. After completion of the reaction, the reaction mixture was quenched by addition of ice cold water (30 g). The reaction mass was further heated to 45-50° C. under stirring for 1 h. The precipitate obtained was filtered and dried under reduced pressure to obtain 5-bromo-7-methylindoline-2,3-dione (2.7 g, 11 mmol $^1$H-NMR (DMSO-$d_6$, 400 MHz): 11.17 (s, 1H), 7.53 (d, J=7.6 Hz, 1H), 7.19 (d, J=7.6 Hz, 1H), 2.19 (s, 3H). MS: m/z=241 [M+H]

Example-9: Preparation of ethyl 3-oxo-3-(o-tolylamino) propanoate and $N^1$,$N^3$-di-o-tolylmalonamide A solution of o-toluidine (50 g, 467 mmol) in toluene (100 g) was added drop wise and under stirring during a period of 5 h to diethyl malonate (523 g, 3266 mmol) at 148° C. After completion of the reaction, excess diethyl malonate was evaporated to obtain a mixture of ethyl 3-oxo-3-(o-tolylamino)propanoate) (89%, 407 mmol) and $N^1$,$N^3$-di-o-tolylmalonamide (11%) (101 g).

Ethyl 3-oxo-3-(o-tolylamino)propanoate): $^1$H-NMR (400 MHz, DMSO-$d_6$) δ 9.53 (s, 1H), 7.40 (d, J=8.0 Hz, 1H), 7.20 (d, J=7.6 Hz, 1H), 7.18-7.10 (m, 1H), 7.08 (dd, $J_1$=7.3 Hz, $J_2$=1.2 Hz, 1H), 4.12 (q, J=7.1 Hz, 2H), 3.48 (s, 2H), 2.20 (s, 3H), 1.2 (t, J=7.1 Hz, 3H); MS: m/z=222.05 [M+H]$N^1$, $N^3$-di-o-tolylmalonamide: $^1$H-NMR (400 MHz, DMSO- $d_6$) δ 9.70 (s, 2H), 7.50 (d, J=5.2 Hz, 2H), 7.08-7.20 (m, 6H), 3.63 (s, 2H), 2.23 (s, 6H); MS: m/z=283.10 [M+H]

Example-10: Preparation of ethyl 2-(hydroxyimino)-3-oxo-3-(o-tolylamino)propanoate and 2-(hydroxyimino)-$N^1$,$N^3$-di-o-tolylmalonamide To a mixture of ethyl 3-oxo-3-(o-tolylamino)propanoate and $N^1$,$N^3$-di-o-tolylmalonamide (101 g) in ethanol (501 g), conc. hydrochloric acid (195 mL, 2054 mmol) was added under stirring, followed by drop wise addition of a solution of sodium nitrite (63 g, 913 mmol in water (100 g)) at −10° C. The resulting suspension was stirred at 25° C. for further 12 h. After completion of the reaction, the solvent was distilled off. Ice cold water (1000 g) was added to the resulting suspension. The precipitated product was filtered and dried under reduced pressure to obtain a mixture of ethyl 2-(hydroxyimino)-3-oxo-3-(o-tolylamino)propanoate (83%) and 2-(hydroxyimino)- $N^1$,$N^3$-di-o-tolylmalonamide (13%)

Ethyl 2-(hydroxyimino)-3-oxo-3-(o-tolylamino)propanoate: $^1$H-NMR (400 MHz, DMSO-$d_6$) δ $^1$H-NMR δ 12.86 & 12.84 (s, 1H), 9.98 & 9.65 (s, 1H), 7.39 (d, J=7.8 Hz, 1H), 7.12-7.27 (m, 3H), 4.28 (q, $J_1$=7.1 Hz, 2H), 2.22 (d, J=10.8 Hz, 3H), 1.28 (t, J=7.1 Hz, 3H). MS: m/z=251.05 [M+H] 2-(hydroxyimino)-$N^1$,$N^3$-di-o-tolylmalonamide: $^1$H-NMR (400 MHz, DMSO-$d_6$) δ 12.53 (s, 1H), 9.94 & 9.45 (s, 2H), 7.50 (d, J=7.3 Hz, 1H), 7.39-7.41 (m, 1H), 6.92-7.27 (m, 6H), 2.25 (s, 6H). m/z=312.15 [M+H]

Example-11: Preparation of 7-methylindoline-2,3-dione from mixture of ethyl 2-(hydroxyimino)-3-oxo-3-(o-tolylamino) propanoate and 2-(hydroxyimino)- $N^1$,$N^3$-di-o-tolylmalonamide To a mixture of ethyl-2-(hydroxyimino)-3-oxo-3-(o-tolylamino) propanoate and 2-(hydroxyimino)-$N^1$,$N^3$-di-o-tolylmalonamide (110 g) in ethanol (1650 g), 47% aqueous sodium hydroxide (NaOH) (94 g, 1099 mmol) was added under stirring. The resulting suspension was stirred for further 2 h at 60° C. After completion of the reaction, the excess solvent was distilled off by azeotropic distillation with toluene (150 g). To the resulting suspension, 1,2-dichloroethane (420 g) was added, followed by slow addition of sulphuric acid (388 g, 3956 mmol) at 0° C. over a period of 45 min. The suspension was stirred at 25° C. for 15 h. After completion of the reaction, the reaction mass was poured into ice cold water (2000 g). The solid product obtained was filtered and dispersed in aqueous methanol (8:1, 300 g) at 70° C. The solid product was filtered, dried under reduced pressure to obtain 7-methylindoline-2,3-dione (45 g, 310 mmol).

$^1$H-NMR (400 MHz, DMSO-$d_6$) δ 11.07 (s, 1H), 7.40 (d, J=8 Hz, 1H), 7.31 (d, J=7.6 Hz, 1H), 6.96 (t, J=7.6 Hz, 1H), 2.16 (s, 3H). MS: m/z=162.05 [M+H]

Example-12: Ethyl 3-((4-chloro-2-methylphenyl) amino)-3-oxopropanoate: The Synthesis Procedure was Followed as Described in Example-8

$^1$H-NMR (400 MHz, DMSO-$d_6$) δ 9.59 (s, 1H), 7.45 (d, J=8.6 Hz, 1H), 7.29 (d, J=2.4 Hz, 1H), 7.20-7.23 (dd, $J_1$=8.6 Hz, $J_2$=2.4 Hz, 1H), 4.11 (q, J=7.1 Hz, 2H), 3.49 (s, 2H), 2.22 (s, 3H), 1.19 (t, J=7.1 Hz, 3H). MS: m/z=253.95 [M−2H]

$N^1$,$N^3$-bis(4-chloro-2-methylphenyl)malonamide: −$^1$H-NMR (400 MHz, DMSO-$d_6$) δ 9.71 (s, 2H), 7.57 (d, J=8.6 Hz, 2H), 7.44 (d, J=8.6 Hz, 2H), 7.29 (d, J=2.4 Hz, 2H), 3.59 (s, 2H), 2.23 (s, 6H). MS: m/z=348.95 [M−H]

Example-13: Ethyl 3-((4-chloro-2-methylphenyl) amino)-2-(hydroxyimino)-3-oxopropanoate: The Synthesis Procedure Followed as Described in Example-9

$^1$H-NMR (400 MHz, DMSO-$D_6$) δ 12.89-12.94 (br, 1H), 10.05 (s, 1H), 7.40-7.45 (d, J=8.8 Hz, 1H), 7.32-7.35 (d, J=2.4 Hz, 1H), 7.23-7.27 (dd, $J_1$=8.8 Hz, $J_2$=2.4 Hz, 1H), 4.24 (q, J=7.2 Hz, 2H), 2.25 (s, 3H), 1.18 (t, J=7.2 Hz, 3H) MS: m/z=285.05 [M+H]

$N^1$, $N^3$-bis (4-chloro-2-methylphenyl)-2-(hydroxyimino) malonamide: −$^1$H-NMR (400 MHz, DMSO-$d_6$) δ 12.83 (s, 1H), 9.44 (s, 2H), 7.50 (d, J=8.8 Hz, 2H), 7.37 (d, J=2.4 Hz, 2H), 7.23 (dd, $J_1$=8.8 Hz, $J_2$=2.4 Hz, 2H), 2.25 (6H). MS: m/z=380.00 [M+H]

Example-14: 5-chloro-7-methylindoline-2, 3-dione The synthesis procedure was followed as described in example-11. $^1$H-NMR (400 MHz, DMSO-$d_6$) δ 11.18 (s, 1H), 7.48 (d, J=2 Hz, 1H), 7.35 (d, J=2 Hz, 1H), 2.16 (s, 3H). MS: m/z=193.90 [M−H]

Example-15: Synthesis of 2-chloro-N-(o-tolyl)acetamide

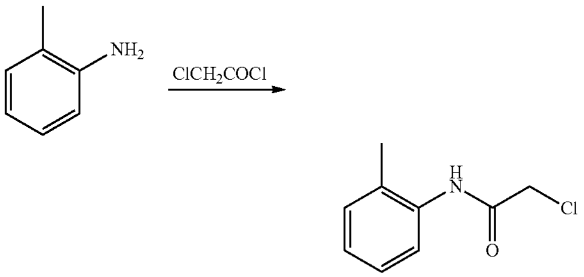

Process-1

To a solution of o-toluidine (1 g, 9.33 mmol) in acetonitrile (10 g), lithium hydroxide monohydrate (0.39 g, 9.33 mmol) was added under stirring, followed by slow addition of 2-chloroacetyl chloride (1.159 g, 10.27 mmol) at 0-5° C. The reaction mixture was stirred for 1 h. After completion of the reaction, the solvent was distilled off and water (5 mL) was added. The precipitated product was filtered and dried under reduced pressure to obtain 2-chloro-N-(o-tolyl)acetamide (1.6 g, 8.71 mmol).

Process-2

To a solution of o-toluidine (100 g, 933 mmol) in ethylene dichloride (500 g), triethyl amine (105 g, 1036 mmol) was added under stifling, followed by the addition of 2-chloroacetyl chloride (117 g, 1036 mmol) at 0-5° C. over a period of 60 min. The reaction mixture was stirred at 20-25° C. for 2 h. After completion of the reaction, the solvent was evaporated and water (400 g) was added. The precipitated product was filtered and dried under reduced pressure to obtain 2-chloro-N-(o-tolyl)acetamide (142 g, 773 mmol).

$^1$H-NMR (400 MHz, DMSO-$d_6$) δ 9.70 (s, 1H), 7.38 (d, J=7.6 Hz, 1H), 7.22 (d, J=7.6 Hz, 1H), 7.17 (t, J=7.6, 1H), 7.10 (t, J=7.6, 1H), 4.29 (s, 2H), 2.19 (s, 3H). MS: m/z=184.00[M+H]

Example-16: Synthesis of 7-methylindolin-2-One

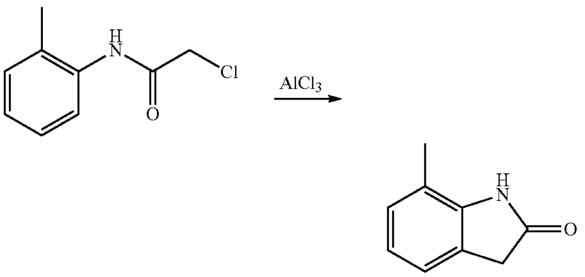

To a stirred melt of aluminium chloride (83 g, 626 mmol), 2-chloro-N-(o-tolyl)acetamide (50 g, 272 mmol) was added portion wise followed by gradually heating the reaction mixture to 190-200° C. The reaction was maintained at the same temperature for 12 h. After completion of the reaction, the reaction mass was poured into ice cold 10% aq. hydrochloric acid (300 mL), and extracted with ethyl acetate (300 g). The organic layer was concentrated to obtain a residue of 7-methylindolin-2-one (28 g, 272 mmol)

$^1$H-NMR (DMSO-$d_6$, 400 MHz): 9.70 (s, 1H), 7.01 (d, J=7.2 Hz, 1H), 6.95 (d, J=7.6 Hz, 1H), 6.82 (t, J=7.2 Hz, 1H), 3.30 (s, 2H), 2.13 (s, 3H). MS: m/z=148.00[M+H]

Example-17: Synthesis of 5-chloro-7-methylindolin-2-One

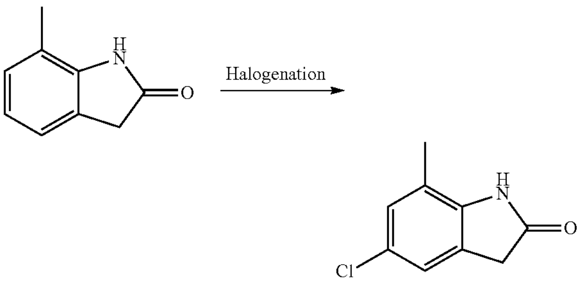

To a stirred solution of 7-methylindolin-2-one (26 g, 177 mmol) in dichloromethane (260 g), a solution of sulfuryl chloride (31 g, 230 mmol) in dichloromethane (50 g) was added at 0-5° C. over a period of 2 h. The reaction mixture was stirred at 8-10° C. for 8 h. After completion of the reaction, the organic layer was separated, washed with 5% aq. sodium bicarbonate (50 g), dried over anhydrous sodium sulphate and concentrated under reduced pressure to obtain 5-chloro-7-methylindolin-2-one (22 g, 177 mmol)

$^1$H-NMR (DMSO-D6, 400 MHz): 10.52 (s, 1H), 7.05-7.07 (d, 2H), 4.18 (s, 2H), 2.13 (s, 3H); MS: m/z=179.95 [M−H]

Example-18: Synthesis of 5-chloro-7-methylindoline-2,3-dione

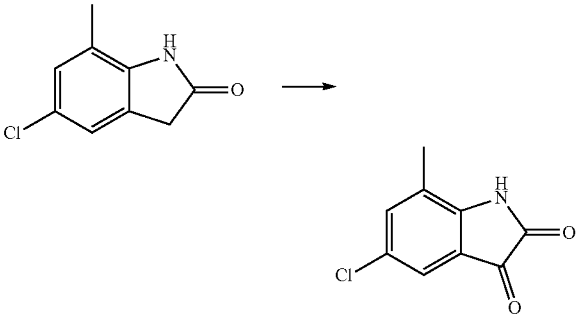

To a stirred solution of 5-chloro-7-methylindolin-2-one (5 g, 27.5 mmol) in acetonitrile (50 g) in an autoclave, $Cu(OAc)_2$ (0.30 g, 1.65 mmol) was added and the reaction vessel was pressurised with oxygen gas (1 bar). The reaction mixture was heated and stirred at 55-60° C. for 2 h. After completion of the reaction, $Cu(OAc)_2$ was removed by filtration through a celite bed and the filtrate was concentrated. The residue obtained was re-dissolved in dichloromethane (30 mL) and washed with 2% aq. citric acid solution (20 mL), dried over anhydrous sodium sulphate and concentrated under reduced pressure to obtain 5-chloro-7-methylindoline-2,3-dione in quantitative yield.

$^1$H-NMR (400 MHz, DMSO-$d_6$) δ 11.18 (s, 1H), 7.48 (d, J=2 Hz, 1H), 7.35 (d, J=2 Hz, 1H), 2.16 (s, 3H). MS: m/z=194 [M−H]

Example-19: Synthesis of 6-chloro-8-methyl-2H-benzo[d][1,3]oxazine-2,4(1H)-dione

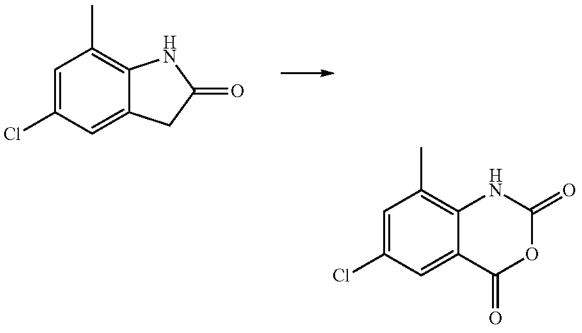

To a stirred suspension of 5-chloro-7-methylindolin-2-one (5 g, 27.5 mmol) and potassium carbonate (0.228 g, 1.65 mmol) in acetonitrile (50 g), cupric acetate monohydrate (0.30 g, 1.65 mmol) and potassium carbonate (0.228 g, 1.65 mmol) were added. 30% Aq. hydrogen peroxide (2.53 mL, 41.3 mmol) was added slowly to the reaction mixture at 25-30° C. The reaction mixture was stirred at 55-60° C. for 12 h. After completion of the reaction, the suspension was filtered and washed with acetonitrile (20 g). Excess solvent was evaporated under reduced pressure. The crude material which was left was dissolved in a mixture of acetic acid (30 g) and sulphuric acid (0.027 mL, 0.51 g). To the resulting suspension, 30% aq. hydrogen peroxide (1.723 mL, 28.1 mmol) was added over a period of 15 min under stirring. The reaction mixture was heated up to 70° C. and maintained at the same temperature for 2 h. After completion of the reaction, the reaction mixture was cooled to 25-30° C. and poured in to ice cold water. The precipitated product was filtered and dried to obtain 6-chloro-8-methyl-2H-benzo[d][1,3]oxazine-2,4(1H)-dione (3.65 g, 17.49 mmol) as brown coloured solid.

$^1$H-NMR (DMSO-$d_6$, 400 MHz): 11.16 (s, 1H), 7.71 (d, J=2.4 Hz, 1H), 7.71 (d, J=2.4 Hz, 1H), 7.66 (d, d, J=2.4 Hz, 1H), 2.31 (s, 3H), MS: m/z=209.95 [M−H].

Example-20: Synthesis of 2-amino-5-chloro-3-methylbenzoic acid

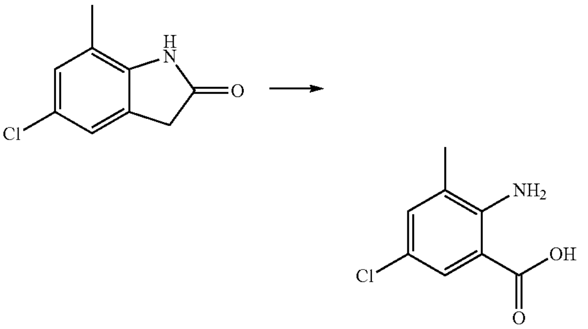

To a stirred solution of 5-chloro-7-methylindolin-2-one (5 g, 27.5 mmol) in acetonitrile (50 g), cupric acetate monohydrate (0.30 g, 1.65 mmol) and potassium carbonate (0.228 g, 1.65 mmol) were added, followed by slow addition of 30% aq. hydrogen peroxide (2.53 mL, 41.3 mmol) at 25-30° C. The reaction mixture was stirred at 55-60° C. for 12 h. Further 30% aq. hydrogen peroxide (2.53 mL, 41.3 mmol) was added, and the mixture was maintained at the same temperature for additional 3 h. 47% Aq. sodium hydroxide (NaOH) (3.5 g, 41 mmol) was added, and the reaction was maintained at 55-60° C. for further 3 h. After completion of the reaction, the solvent was evaporated. To the residue, water (20 mL) and ethyl acetate (20 mL) were added. The aqueous layer was separated from the organic layer and acidified (pH to 3.8) with aq. hydrochloric acid and extracted with ethyl acetate (3×20 ml). The combined organic layers were dried over anhydrous sodium sulphate and concentrated under reduced pressure to obtain 2-amino-5-chloro-3-methylbenzoic acid (3.5 g, 18.9 mmol).

$^1$H-NMR (DMSO-$d_6$, 400 MHz): 11.17 (s, 1H), 7.55 (d, J=2 Hz, 1H), 7.20 (d, J=2 Hz, 1H), 2.09 (s, 3H); MS: m/z=184 [M−H]

Example-21: Synthesis of ethyl 2-oxo-2-(o-tolylamino)acetate

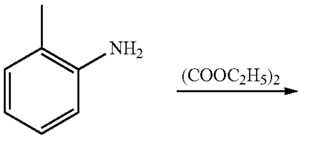

-continued

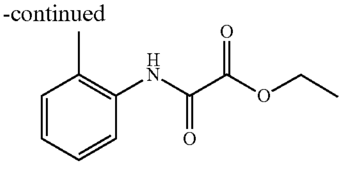

To preheated diethyl oxalate (126 mL, 924 mmol), o-toluidine (30 g, 280 mmol) was added at 150° C. under stirring. The reaction was maintained at 150° C. for 6 h. After completion of the reaction, excess diethyl oxalate was distilled off to obtain ethyl 2-oxo-2-(o-tolylamino)acetate (52 g, 280 mmol).

$^1$H-NMR (400 MHz, DMSO-$d_6$) δ 10.27 (s, 1H), 7.33 (dd, $J_1$=7.6 Hz, $J_{2=1.6}$ Hz, 1H), 7.27 (dd, $J_1$=6.8 Hz, $J_2$=1.6 Hz, 1H), 7.23-7.14 (m, 2H), 4.12 (q, J=6.8 Hz, 2H), 2.18 (s, 3H), 1.31 (t, J=7.2 Hz, 3H); LCMS m/z=208.00 [M+H].

Example-22: Synthesis of 2-morpholino-2-oxo-N-(o-tolyl)acetamide

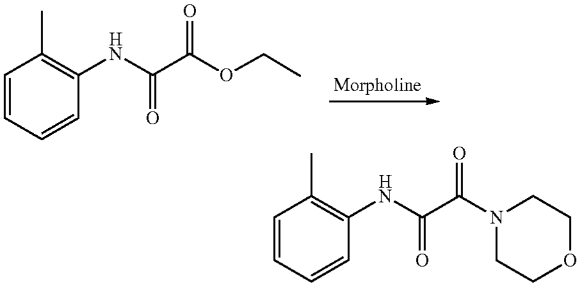

Ethyl 2-oxo-2-(o-tolylamino)acetate (10 g, 48.3 mmol) was added to morpholine (21.02 mL, 241 mmol), and the reaction mixture was heated to 125-130° C. under stirring for 6 h. After completion of the reaction, excess morpholine was distilled off, and the residue was treated with n-hexane (50 g). The product was isolated by filtration, dried under reduced pressure to obtain 2-morpholino-2-oxo-N-(o-tolyl) acetamide (11.50 g, 46.3 mmol,);

$^1$H-NMR (400 MHz, DMSO-$d_6$): δ 10.21 (s, 1H), 7.39 (dd, $J_1$=8 Hz, $J_2$=1.2 Hz, 1H), 7.28-7.11 (m, 3H), 3.64 (t, J=4.8 Hz, 4H), 3.55 (t, J=4.4 Hz, 4H), 2.04 (s, 3H); LCMS m/z=247.03 [M−H].

Example-23: Synthesis of 7-methylindoline-2,3-dione

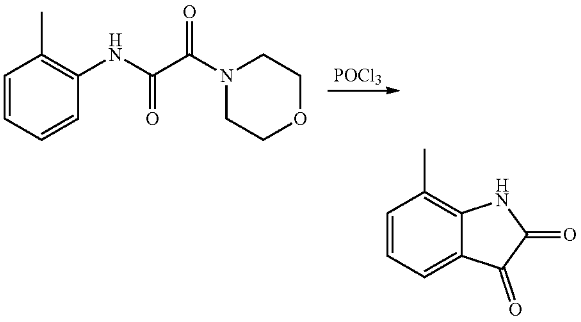

Phosphorus oxychloride ($POCl_3$) (1.877 mL, 20.14 mmol) was added dropwise and under stirring to 2-morpholino-2-oxo-N-(o-tolyl)acetamide (0.5 g, 2.014 mmol). The reaction mixture was heated to 60° C., and stirring was continued for 16 h. After completion of the reaction, the reaction mixture was poured into ice cold water (50 g) and extracted with ethyl acetate (3×20 ml). The combined organic layers were washed with 10% aq. $NaHCO_3$ (20 g), dried over anhydrous sodium sulphate and concentrated under reduced pressure to obtain 7-methylindoline-2,3-dione.

$^1$H-NMR (400 MHz, DMSO-$d_6$) δ 11.07 (s, 1H), 7.32 (d, J=7.6 Hz, 1H), 7.24 (d, J=7.6 Hz, 1H), 6.90 (t, J=8 Hz, 1H), 2.17 (s, 3H). MS: m/z=162.05 [M+H].

Example-24: Synthesis of N$^1$-(o-tolyl)oxalamide

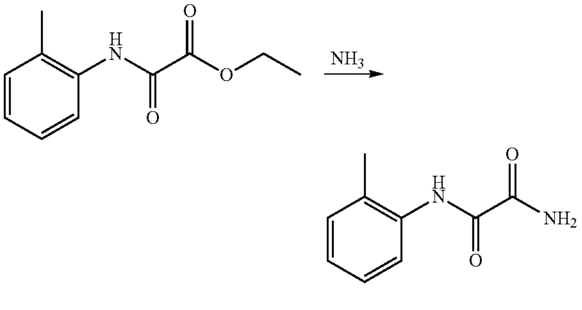

Into a stirred suspension of ethyl 2-oxo-2-(o-tolylamino) acetate (5 g, 24.13 mmol) in methanol (20 g), ammonia gas was purged for 20-30 min at 20-25° C. The reaction mixture was stirred at the same temperature for 12 h. After completion of reaction, the excess solvent was distilled off and n-hexane (20 g) was added. The precipitated product was filtered and dried under reduced pressure to obtain N$^1$-(o-tolyl)oxalamide (3.5 g, 19.64 mmol);

$^1$H-NMR (DMSO-$d_6$, 400 MHz): 9.99 (s, 1H), 8.29 (bs, 1H), 7.99 (bs, 1H), 7.50 (d, J=8 Hz, 1H), 7.25-7.10 (m, 3H), 2.20 (s, 3H); LCMS: m/z=177.05 [M−1].

Example-25: Synthesis of o-tolylcarbamoyl cyanide

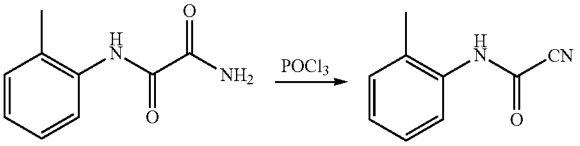

To a stirred solution of N$^1$-(o-tolyl)oxalamide (5 g, 28.1 mmol) in dichloroethane (50 mL), phosphorus oxychloride ($POCl_3$) (10.46 mL, 112 mmol) was added. The reaction mixture was heated to 80° C. and maintained at this temperature for 16 h. After completion of the reaction, the reaction mixture was poured into ice cold water (20 mL) and extracted with ethyl acetate (20 mL). The organic layer was evaporated under reduced pressure to obtain o-tolylcarbamoyl cyanide (3.6 g, 22 mmol).

$^1$H-NMR (DMSO-$d_6$, 400 MHz): 11.32 (s, 1H), 7.37-7.33 (m, 1H), 7.29-7.60 (m, 1H), 7.24-7.19 (m, 1H), 2.21 (s, 3H); LCMS: m/z=159.05 [M−1].

Example-26: Synthesis of 7-methylindoline-2,3-dione

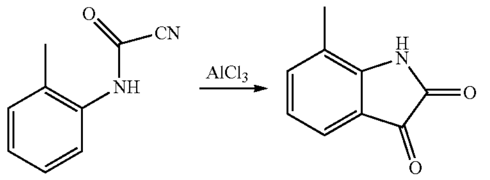

To a stirred solution of o-tolylcarbamoyl cyanide (1 g, 6.24 mmol) in m-chlorobenzene (3 g), aluminium chloride (1 g, 7.49 mmol) was added, and the mixture was heated gradually to 110° C. and maintained at this temperature for 5 h. After completion of the reaction, the reaction mixture was poured into ice cold water (10 mL) and extracted with ethyl acetate (3×20 ml). The combined organic layers were washed with water (10 mL), dried over anhydrous sodium sulphate and concentrated under reduced pressure to obtain 7-methylindoline-2,3-dione (0.6 g, 3.75 mmol).

$^1$H-NMR (DMSO-$d_6$, 400 MHz): 11.07 (s, 1H), 7.32 (d, J=7.6 Hz, 1H), 7.24 (d, J=7.6 Hz, 1H), 6.90 (t, J=8 Hz, 1H), 2.17 (s, 3H); MS: m/z=162.05 [M+H].

Example-27: Synthesis of 2-(hydroxyimino)acetic Acid

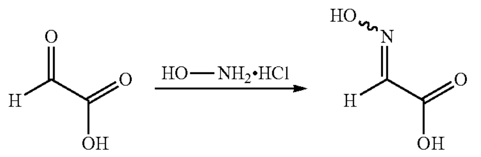

Hydoxylamine hydrochloride (46.9 g, 675 mmol) was added to a stirred 50% aqueous solution of glyoxylic acid (100 g, 675 mmol) at 5-10° C. The reaction mass was stirred at 15-20° C. for 6 h and then cooled to 5-10° C. The solid which was obtained was filtered to afford 2-(hydoxyimino) acetic acid (48 g, 539 mmol).

$^1$H-NMR (DMSO-$d_6$, 400 MHz): 12.90 (bs, 1H), 12.35 (bs, 1H), 7.42 (s, 1H).

Example-28: Synthesis of methyl-2-(hydroxyimino)acetate

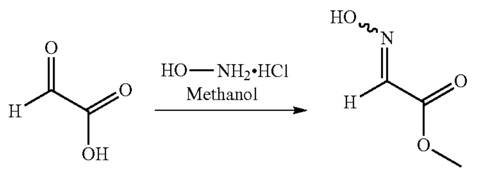

To a stirred solution of 50% aqueous glyoxylic acid (100 g, 675 mmol) in methanol (500 g), hydoxylamine hydrochloride (49.6 g, 675 mmol) was added at 5-10° C. The reaction mixture was stirred at 15-20° C. for 4 h. Excess methanol was distilled off, and the reaction mixture was cooled to 5-10° C. The solid obtained was filtered to obtain 2-(hydoxyimino) acetic acid (50 g, 785 mmol).

$^1$H-NMR (DMSO-$d_6$, 400 MHz): 12.90 (bs, 1H), 12.35 (bs, 1H), 7.42 (s, 1H); GCMS: m/z=103.

Example-29: Synthesis of methyl-2-(methoxyimino)acetate

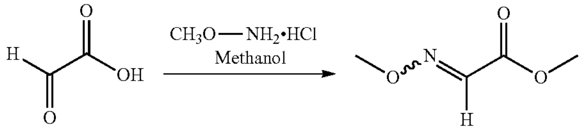

To a stirred solution of 50% aqueous glyoxylic acid (40 g, 270 mmol) in methanol (200 g), methoxyamine hydrochloride (22.56 g, 270 mmol) was added at 5-10° C. The reaction mixture was stirred at 15-20° C. for 4 h. Excess methanol was distilled off. The reaction mixture was extracted with dichloromethane (60 g) and the extract was concentrated under reduced pressure to obtain methyl-2-(methoxyimino) acetate (22 g, 188 mmol).

$^1$H-NMR (DMSO-$d_6$, 400 MHz): 7.6 (s, 1H), 3.95 (s, 3H), 3.73 (s, 3H); GCMS: m/z=117.

Example-30: Synthesis of methyl-2-(methoxyimino)acetate

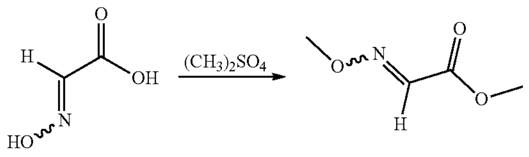

Process-1

To a stirred solution of 2-(hydroxyimino) acetic acid (10 g, 97 mmol, 1.0 eq.) in acetone (100 g), potassium carbonate (16.09 g, 109 mmol) was added at 5-10° C. Stirring was continued for 1 h at 5-10° C. Now, dimethyl sulfate (12.24 g, 97 mmol) was added slowly under stirring over a period of 30 min at 5-10° C. The reaction mixture was stirred at 15-20° C. for further 12 h. The suspension was filtered and the filtrate was evaporated to obtain methyl 2-(methoxyimino)acetate (9 g, 77 mmol).

Process-2

To tetrahydrofuran (5 mL), 2-(hydroxyimino) acetic acid (0.5 g, 5.61 mmol, 1.0 eq) and potassium hydroxide (0.81 g, 12.35 mmol, 2.2 eq) were added at 5-10° C. under stirring. The reaction mixture was stirred at 5-10° C. for further 1 h. Now, dimethyl sulphate (0.85 g, 6.74 mmol, 1.2 eq) was added slowly over a period of 30 min at 5-10° C. under stirring. The reaction mixture was stirred further at 15-20° C. for 12 h. After completion of the reaction, the reaction mixture was filtered and the filtrate was concentrated under reduced pressure to obtain methyl-2-(methoxyimino)acetate (0.5 g, 4.27 mmol).

$^1$H-NMR (DMSO-$d_6$, 400 MHz): 7.6 (s, 1H), 3.95 (s, 3H), 3.73 (s, 3H); GCMS: m/z=117.

Example-31: Synthesis of 2-(methoxyimino)-N-(o-tolyl)acetamide

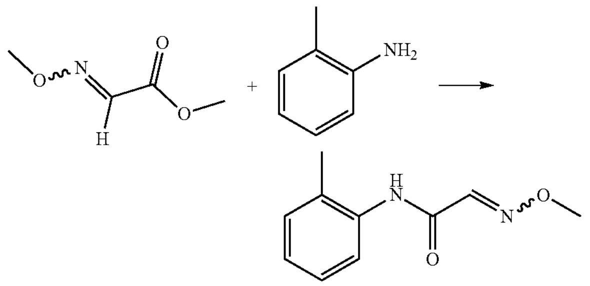

In a reaction tube, o-toluidine (0.91 g, 8.54 mmol, 1.0 eq) and methyl 2-(methoxyimino)acetate (1.0 g, 8.54 mmol, 1.0 eq) were mixed together at 25-30° C. The tube was sealed, heated up to 120-125° C. and stirred at the same temperature for 12 h. The reaction vessel was cooled to 25-30° C. to obtain crude 2-(methoxyimino)-N-(o-tolyl)acetamide (1.4 g, 7.28 mmol).

$^1$H-NMR (DMSO-$d_6$, 400 MHz): 9.69 (s, 1H), 7.80 (s, 1H), 7.4 (d, J=7.6 Hz, 1H), 7.2 (d, J=7.2 Hz, 1H), 7.18 (t, J=7.6 Hz, 1H), 7.12 (t, J=7.6 Hz, 1H), 3.96 (s, 3H), 2.20 (s, 3H); GCMS: m/z=192.

Example-32: Synthesis of 2-(hydroxyimino)acetic acid

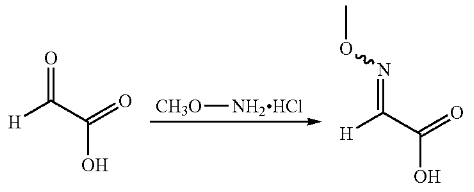

To a 50% aqueous solution of glyoxylic acid (20 g, 135 mmol), methoxy amine hydrochloride (11.84 g, 142 mmol) was added at 5-10° C. The reaction mixture was stirred at 15-20° C. for 6 h. After completion of the reaction, the reaction mixture was cooled to 5-10° C. and filtered to obtain 2-(hydoxyimino) acetic acid (10.2 g, 99 mmol).

$^1$H-NMR (DMSO-$d_6$, 400 MHz): 13.2 (br, 1H), 7.5 (s, 1H), 3.9 (s, 3H).

Example-33: Synthesis of 2-(methoxyimino)-N-(o-tolyl)acetamide

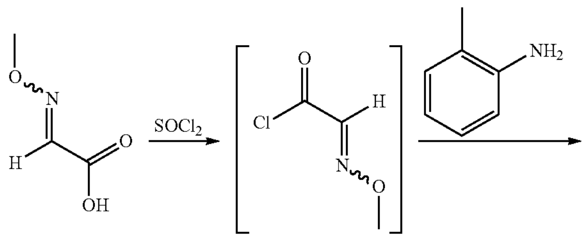

-continued

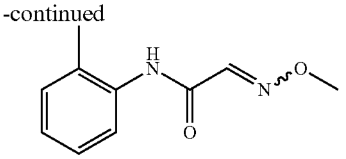

To a stirred solution of 2-(methoxyimino)acetic acid (9.5 g, 92 mmol) in dichloroethane (4 g), thionyl chloride (8.07 mL, 111 mmol) was added at 0-5° C. The reaction mixture was stirred for 2 h to obtain 2-(methoxyimino)acetyl chloride, which was dissolved in dichloroethane (5 g). o-Toluidine (10.86 g, 101 mmol) was added to this reaction mixture, followed by the addition of triethylamine (32.1 ml, 230 mmol) at 0-5° C. The resulting suspension was stirred for 1 h at 0-5° C. then at 25-30° C. for further 12 h. The reaction mixture was poured in ice cold water (30 g) and extracted with dichloroethane (10 g). The organic layer was concentrated under reduced pressure to obtain 2-(methoxyimino)-N-(o-tolyl)acetamide (15 g, 78 mmol).

$^1$H-NMR (DMSO-$d_6$, 400 MHz): 9.69 (s, 1H), 7.80 (s, 1H), 7.4 (d, J=7.6 Hz, 1H), 7.2 (d, J=7.2 Hz, 1H), 7.20-7.16 (t, J=7.6 Hz, 1H), 7.14-7.10 (t, J=7.6 Hz, 1H), 3.96 (s, 3H), 2.20 (s, 3H); GCMS: m/z=192.

Example-34: Synthesis of 7-methylindoline-2,3-dione

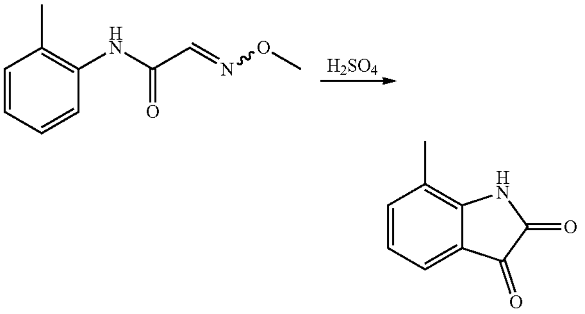

To concentrated sulphuric acid (53.9 g, 550 mmol), 2-(methoxyimino)-N-(o-tolyl)acetamide (14 g, 73 mmol) was added at 0-5° C. The reaction mixture was stirred at 20-25° C. for 12 h. After completion of the reaction, the reaction mixture was quenched by the addition of ice cold water (200 g) to obtain a solid which was filtered to obtain 7-methylindoline-2,3-dione (8 g, 49.6 mmol).

$^1$H-NMR (DMSO-$d_6$, 400 MHz): 11.07 (s, 1H), 7.32 (d, J=7.6 Hz, 1H), 7.24 (d, J=7.6 Hz, 1H), 6.90 (t, J=8 Hz, 1H), 2.17 (s, 3H). MS: m/z=162.05 [M+H].

Example-35: Synthesis of 5-chloro-7-methylindoline-2,3-dione

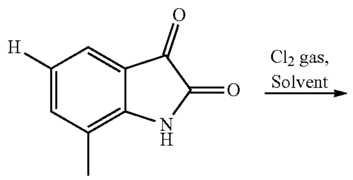

-continued

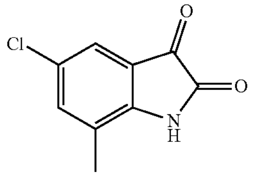

Process-1

Into a stirred solution of 7-methylindoline-2,3-dione (67.0 g, 0.42 mol) in N-methylpyrrolidone (150 g), chlorine gas (81.0 g, 1.15 mol) was purged at 45° C. After 30 min, 2-propanol (225 g) was added at 50-55° C. to the resulting suspension over a period of 5-10 min. The reaction mixture was cooled to 25-30° C. The solid product was filtered, washed with 2-propanol (75 g), water (75.0 g) and dried under reduced pressure to obtain 5-chloro-7-methylindoline-2,3-dione (65 g, 0.33 mol).

Process-2

To a stirred solution of 7-methylindoline-2,3-dione (10 g, 68 mmol) in N,N-dimethylformamide (30 g), chlorine gas was purged for 30 min at 50-70° C. The reaction mixture was cooled to 25-30° C., after which 2-propanol (80 g) was added. The reaction mixture was further cooled to 5-10° C. The solid product was filtered, washed with water (10 g) and 2-propanol (10 g) and dried under reduced pressure to obtain 5-chloro-7-methylindoline-2,3-dione (9 g, 46 mmol)

$^1$H-NMR (400 MHz, DMSO-$d_6$) δ 11.18 (s, 1H), 7.48(d, J=2 Hz, 1H), 7.35 (d, J=2 Hz, 1H), 2.16 (s, 3H). MS: m/z=193.90 [M−H]

Example-36: Synthesis of 6-chloro-8-methyl-2H-benzo[d][1,3]oxazine-2,4(1H)-dione

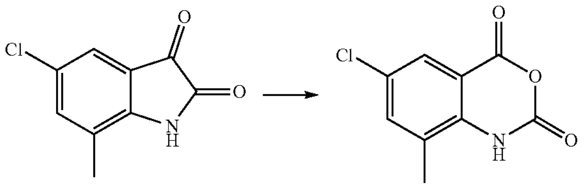

Process-1

To a stirred solution of 5-chloro-7-methylindoline-2,3-dione (61.3 g, 314 mmol) in N-methylpyrrolidone (315 g), selenous acid was added as catalyst (2 g, 15.7 mmol) at 25° C. To this reaction mixture, aqueous hydrogen peroxide (68.1 mL, 941 mmol, 47.0% w/w) was added drop wise at 25° C. during a period of 15 min. The reaction mixture was stirred at 45° C. for 12 h. After completion of the reaction, the reaction mixture was cooled to −5° C., followed by the addition of 2-propanol (630 g). The precipitated product was filtered, washed with water (50 g) and 2-propanol (50 g) and dried to obtain 6-chloro-8-methyl-2H-benzo[d][1,3]oxazine-2,4(1H)-dione (56.4 g, 266 mmol).

Process-2

To a stirred solution of 5-chloro-7-methylindoline-2,3-dione (18.9 g, 96.0 mmol) in N-methylpyrrolidone (NMP)

(195 mL), selenous acid was added as catalyst (0.6 g, 4.8 mmol) at 25° C. To this reaction mixture, aqueous hydrogen peroxide (21.6 mL, 289 mmol, 41.0% w/w) was added drop wise at 25° C., during a period of 15 min. The reaction mixture was stirred at 45° C. for 2 h, and then cooled to 25° C. The reaction mixture was then poured into ice-cold water (600 mL) under stirring. The solid precipitate was filtered, washed with water (50 mL) and dried to obtain 6-chloro-8-methyl-2H-benzo[d][1,3]oxazine-2,4(1H)-dione (18.2 g, 86.1 mmol).

Process-3

To a stirred solution of 5-chloro-7-methylindoline-2,3-dione (8.9 g, 45.4 mmol) in tetrahydrofuran (90 mL), selenous acid was added as catalyst (0.3 g, 2.3 mmol) at 25° C. To this reaction mixture, aqueous hydrogen peroxide (9.8 mL, 136 mmol, 40% w/w) was added drop wise at 25° C. during a period of 15 min. The reaction mixture was stirred at 45° C. for 16 h and then cooled to 25° C. The reaction mixture was further cooled to −10° C. The solid precipitate was filtered and dried to obtain 6-chloro-8-methyl-2H-benzo[d][1,3]oxazine-2,4(1H)-dione (8.2 g, 38.8 mmol).

Process-4

To a stirred solution of 5-chloro-7-methylindoline-2,3-dione (492 g, 2515 mmol) in ethyl acetate (2332 mL), selenous acid was added as catalyst (17.47 g, 126 mmol) at 25° C. To this reaction mixture, aqueous hydrogen peroxide (559 mL, 7556 mmol, 46% w/w) was added drop wise at 25° C. during 1.5 h. The reaction mixture was stirred for 15 h at 45° C. and then cooled to 0° C. Excess hydrogen peroxide was quenched by addition of aq. sodium thiosulfate pentahydrate. The solid precipitate was filtered under vacuum and dried to obtain 6-chloro-8-methyl-2H-benzo[d][1,3]oxazine-2,4(1H)-dione (463.5 g, 2190 mmol,).

Process-5

To a stirred solution of 5-chloro-7-methylindoline-2,3-dione (1.0 g, 5.1 mmol) in a mixture of dimethyl formamide and acetonitrile (1:1, 5 mL), selenium dioxide (0.03 g, 0.3 mmol) was added as catalyst, followed by the addition of acetic acid (0.2 g, 2.6 mmol) at 25° C. Aqueous hydrogen peroxide (0.9 mL, 15.3 mmol, 48% w/w) was added drop wise at 25° C. during a period of 5 min. The reaction mixture was stirred at 45° C. for 16 h and then cooled to 5° C. The solid precipitate was filtered, washed with water (10 mL) and dried to obtain 6-chloro-8-methyl-2H-benzo[d][1,3]oxazine-2,4(1H)-dione (0.8 g, 5.1 mmol).

Process-6

To a stirred solution of 5-chloro-7-methylindoline-2,3-dione (1.0 g, 5.1 mmol) in a mixture of dimethyl formamide and acetonitrile (1:1, 5 mL), selenous acid was added as catalyst (0.03 g, 0.23 mmol), followed by acetic acid (0.15 g, 2.6 mmol) at 25° C. Aqueous hydrogen peroxide (1.26 mL, 15.34 mmol, 35% w/w) was added drop wise at 25° C. during a period of 5 min. The reaction mixture was stirred at 45° C. for 16 h and then cooled to 5° C. The solid precipitate was filtered, washed with water (10 mL) and dried to obtain 6-chloro-8-methyl-2H-benzo[d][1,3]oxazine-2,4(1H)-dione (0.9 g, 4.3 mmol).

Process-7

To a stirred solution of 5-chloro-7-methylindoline-2,3-dione (1.0 g, 5.1 mmol) in DMF/ACN (5 mL), tungstic acid (0.06 g, 0.3 mmol) and acetic acid (0.2 g, 2.6 mmol) were added at 25° C. Aqueous hydrogen peroxide (0.9 mL, 15.3 mmol, 48% w/w) was added drop wise at 25° C. during a period of 5 min. The reaction mixture was stirred at 45° C. for 16 h and then cooled to 5° C. The solid precipitate was filtered, washed with water (10 mL) and dried to obtain 6-chloro-8-methyl-2H-benzo[d][1,3]oxazine-2,4(1H)-dione (0.6 g, 4.3 mmol).

$^{1}$H-NMR (DMSO-$d_6$, 400 MHz): 11.16 (s, 1H), 7.71 (d, J=2.4 Hz, 1H), 7.71 (d, J=2.4 Hz, 1H), 7.66 (d, d, J=2.4 Hz, 1H), 2.31 (s, 3H), MS: m/z=209.95 [M−H].

Example-37: Synthesis of 2-amino-5-chloro-3-methylbenzoic acid

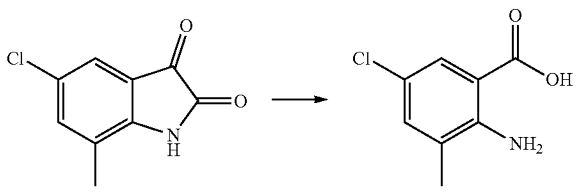

To a stirred solution of 5-chloro-7-methylindoline-2,3-dione (1.0 g, 5.1 mmol) in DMF (5 g), selenous acid was added as catalyst (0.03 g, 0.23 mmol) at 25° C., followed by drop wise addition of aqueous 30% hydrogen peroxide (1.26 mL, 15.34 mmol, 35% w/w) during a period of 5 min. The reaction mixture was stirred for 24 h at 70° C. to obtain 2-amino-5-chloro-3-methylbenzoic acid.

$^{1}$H-NMR (DMSO-$d_6$, 400 MHz): 11.17 (s, 1H), 7.55 (d, J=2 Hz, 1H), 7.20 (d, J=2 Hz, 1H), 2.09 (s, 3H); MS: m/z=184 [M−H].

Example-38: Synthesis of 2-amino-N-(tert-butyl)-5-chloro-3-methylbenzamide

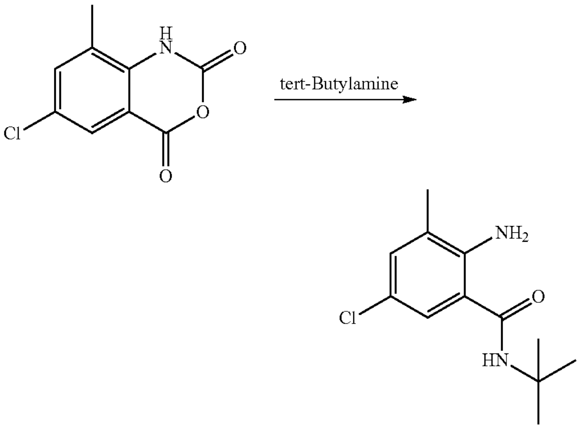

To a stirred suspension of 6-chloro-8-methyl-2H-benzo[d][1,3]oxazine-2,4(1H)-dione (2.00 g, 8.84 mmol) in acetonitrile (10.0 g), pyridine (0.715 mL, 8.84 mmol) was added, followed by the addition of tert-butylamine (1.115 mL, 10.61 mmol) at 15-20° C. The reaction mixture was heated to 70° C. and maintained at this temperature for 24 h. After completion of the reaction, the resulting suspension was quenched by addition of water (10 g) The mixture was extracted with ethyl acetate (20 g), the organic extract was dried over anhydrous sodium sulphate and concentrated under reduced pressure to obtain 2-amino-N-(tert-butyl)-5-chloro-3-methylbenzamide.

$^{1}$H-NMR (400 MHz, DMSO-$d_6$) δ 7.70 (s, 1H), 7.32 (d, J=2.8 Hz, 1H), 7.08 (d, J=0.8 Hz, 1H), 6.05 (bs, 2H), 2.06 (s, 3H), 1.32 (s, 9H); MS: m/z=239.10 [M−1].

Example-39: Synthesis of 2-amino-3-bromo-5-chloro-N-(1-cyclopropylethyl)benzamide

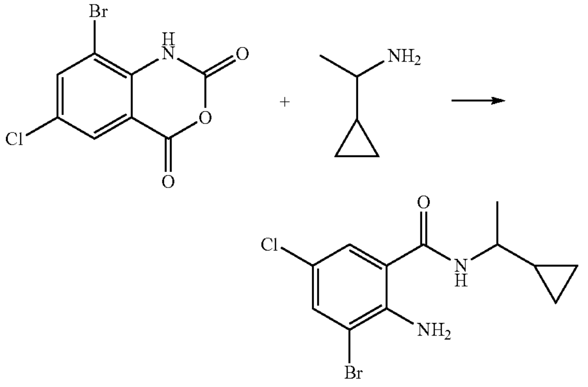

To a stirred solution of 8-bromo-6-chloro-2H-benzo[d][1,3]oxazine-2,4(1H)-dione (0.2, 0.723 mmol) and 1-cyclopropylethan-1-amine hydrochloride (88 mg, 0.723 mmol) in ethanol (2 mL), potassium carbonate (0.150 g, 1.085 mmol) was added, and the reaction mixture was stirred at 24-25° C. for 16 h. After completion of the reaction, the solvent was evaporated. The resulting suspension was dissolved in water (5 mL) and extracted with ethyl acetate (10 mL). The organic layer was concentrated under reduced pressure to obtain 2-amino-3-bromo-5-chloro-N-(1-cyclopropylethyl) benzamine $^{1}$H-NMR (400 MHz, DMSO-$d_6$) δ 8.43 (d, J=8 Hz, 1H), 7.63 (d, J=2.4 Hz, 1H), 7.59 (d, J=2.4 Hz, 1H), 6.52-6.49 (bs, 2H), 3.46-3.38 (dt, J1=8.4 Hz J2=6.8 Hz 1H), 1.18 (d, J=6.4 Hz, 3H), 0.98-1.19 (m, 1H), 0.4-0.48 (m, 1H), 0.34-0.4 (1H), 0.24-0.3 (m, 1H), 0.15-0.2 (m, 1H).

Example-40: Synthesis of 2-chloro-N-(4-chlorophenyl)acetamide

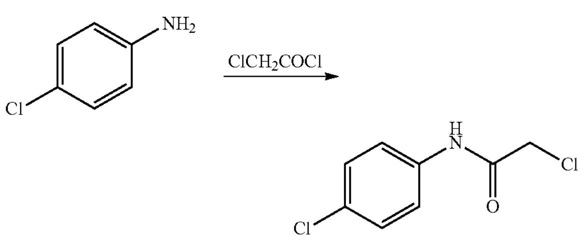

To a stirred solution of 4-chloroaniline (20 g, 157 mmol) in ethylene dichloride (120 g), triethyl amine (31.7 g, 314 mmol) was added at room temperature, followed by the addition of a solution of 2-chloroacetyl chloride (35.4 g, 314 mmol) in ethylene dichloride (20 g) at 0-5° C. during a period of 60 min. The reaction mixture was stirred at 20-25°

C. for 6 h. After completion of the reaction, the solvent was evaporated and water (80 g) was added. The precipitated product was filtered and dried under reduced pressure to obtain 2-chloro-N-(4-chlorophenyl)acetamide (25.6 g, 125 mmol).

$^1$H-NMR (400 MHz, DMSO-$d_6$) δ 10.42 (s, 1H), 7.61 (tt, J=9.2 Hz, 2H), 7.35 (tt, J=8.8 Hz, 2H), 4.24 (s, 2H). MS: m/z=202 [M−H]

Example-41: Synthesis of N-(2-bromo-4-chlorophenyl)-2-chloroacetamide

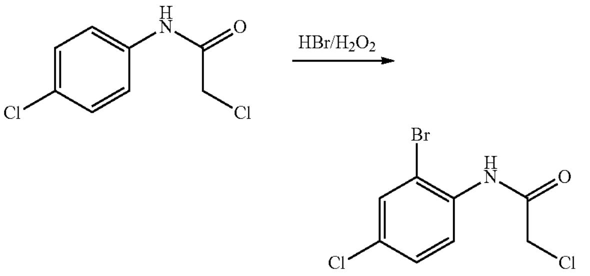

Process-1

To a stirred solution of 2-chloro-N-(4-chlorophenyl)acetamide (2 g, 9.8 mmol) in ethylene dichloride (16 mL), 50% aqueous hydrogen peroxide (1.31 mL, 19.60 mmol) was added followed by slow addition of 46% aqueous hydrobromic acid (2.26 mL, 19.60 mmol) at 0-10° C. The reaction mixture was stirred at 60° C. for 15 h. After completion of the reaction, excess solvent was evaporated under reduced pressure to obtain a residue. To this residue, ice cold water (20 mL) was added. The resulting precipitated product was filtered and dried under reduced pressure to obtain N-(2-bromo-4-chlorophenyl)-2-chloroacetamide (2.21 g, 7.81 mmol).

$^1$HNMR (DMSO-$d_6$, 400 MHz): 9.85 (s, 1H), 7.80 (t, J=2.4 Hz, 1H), 7.7.64 (t, J=8.8 Hz, 1H), 7.48-7.45 (m, $J_1$=2.4 Hz, $J_1$=8.8 Hz, 1H), 4.35 (s, 2H), 2.19 (s, 3H); MS: m/z=282 [M−H]

Process-2

To a stirred solution of 2-chloro-N-(4-chlorophenyl)acetamide (2 g, 9.80 mmol) in ethylene dichloride (16 mL), a solution of bromine (1.01 mL, 19.60 mmol) in ethylene dichloride (1.0 mL, 19.60 mmol) was added slowly at 5-10° C. The reaction mixture was stirred for 15 h at 60° C. After completion of the reaction, excess solvent was evaporated under reduced pressure to obtain a residue. To this residue, water (20 mL) was added. The resulting precipitated product was filtered and dried under reduced pressure to obtain N-(2-bromo-4-chlorophenyl)-2-chloroacetamide (1.66 g, 5.87 mmol).

Process-3

To a stirred solution of 2-chloro-N-(4-chlorophenyl)acetamide (2 g, 9.8 mmol) in ethylene dichloride (16 mL), N-bromosuccinimide (1.19 g, 10.78 mmol) was added at 25° C. The reaction mixture was stirred at 80° C. for 15 h. After completion of the reaction, excess solvent was removed under reduced pressure to obtain a residue. To this residue, water (20 mL) was added. The resulting precipitated product was filtered and dried under reduced pressure to obtain N-(2-bromo-4-chlorophenyl)-2-chloroacetamide (1.65 g, 5.88 mmol).

2-Amino-3-bromo-5-chloro-N-(1-cyclopropylethyl)benzamide is prepared from N-(2-bromo-4-chlorophenyl)-2-chloroacetamide according the process as described in example-8 followed by example-36.

Having described the invention with reference to certain preferred embodiments, other embodiments will become apparent to one skilled in the art from consideration of the specification. It will be apparent to those skilled in the art that many modifications, both to materials and methods, may be practiced without departing from the scope of the invention.

The invention claimed is:

1. A process for the synthesis of a compound of formula (VII), (VII)

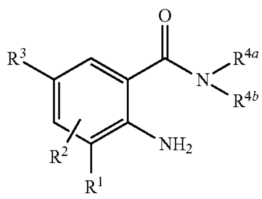

wherein, $R^1$ is selected from the group consisting of halogen, $C_1$-$C_4$ alkyl and $C_3$-$C_4$-cycloalkyl;

$R^2$ is selected from the group consisting of hydrogen, halogen, cyano, $C_1$-$C_4$ alkyl and $C_3$-$C_4$-cycloalkyl;

$R^3$ is selected from the group consisting of hydrogen, halogen, cyano, $C_1$-$C_4$ haloalkyl and $C_3$-$C_6$ cycloalkyl;

$R^{4a}R^{4b}$ wherein $R^{4a}$ and $R^{4b}$ are independently selected from the group consisting of hydrogen, $C_1$-$C_6$ alkyl, $C_3$-$C_6$ cycloalkyl, and $C_3$-$C_6$ cycloalkyl-$C_1$-$C_4$ alkyl;

comprising a) through d)

a) reacting a compound of formula (II) with a compound of formula (III) to afford a compound of formula (IV), optionally in the presence of a base and a solvent;

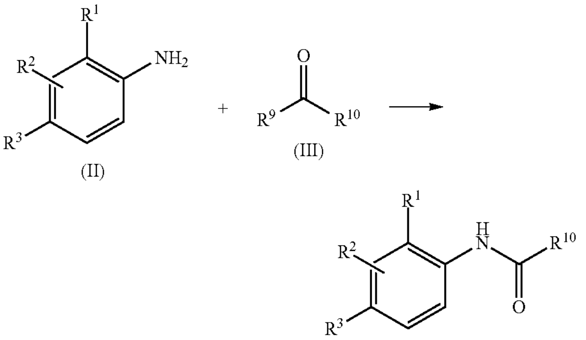

(II) (III) (IV)

wherein, $R^9$ is selected from the group consisting of Cl, Br and $C_1$-$C_4$ alkoxy;

$R^{10}$ is selected from the group consisting of cyano, $CH_2X$, $CH_2$—(C═O)—$OR^a$, $COOR^a$, $C(O)R^c$ and $CR^d$═$NR^e$;

$R^a$ is selected from the group consisting of hydrogen and $C_1$-$C_4$-alkyl, $R^c$ is selected from the group consisting of $N(R^a)_2$ and two $R^a$ together with the atoms to which they are attached or together with further atoms selected from the group consisting of C, N, O, S and optionally including 1 to 3 ring members selected from the group consisting of C(═O), C(═S), $S(O)_m$ and $SiR'_2$ may form a five to six membered non-aromatic ring;

—$R^d$ is selected from the groups consisting of hydrogen, $C_1$-$C_4$-alkyl, (C═O)—$R^a$, $COOR^a$, $CON(R^a)_2$ and phenyl;

$R^e$ is selected from the groups consisting of hydroxy and $C_1$-$C_4$ alkoxy;

X represents halogen;

b) reacting the compound of formula (IV) with an acid to obtain isatin of formula (V), optionally in the presence of a solvent;

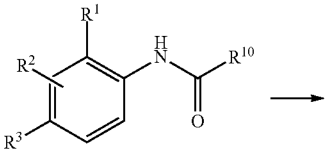

(IV)

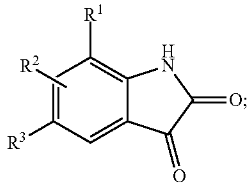

(V)

c) oxidizing the isatin of formula (V) to obtain isatoic anhydride of formula (VI) in presence of a oxidizing agent and a catalyst, optionally in the presence of a solvent;

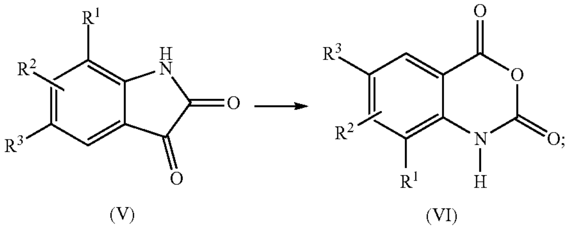

(V) (VI)

or hydrolyzing the isatin of formula (V) to obtain an anthranilic acid of formula (VIIa) in presence of a hydrolysisng agent, optionally in the presence of a solvent;

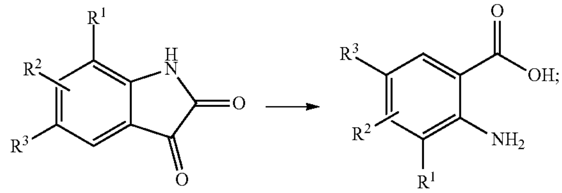

(V) (VIIa)

and d) reacting the compound of formula (VI) with a compound of formula (VIII), to obtain a compound of formula (VII), optionally in the presence of an acid and a solvent; as shown in the following scheme:

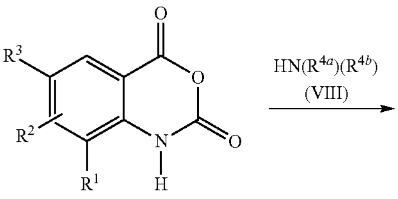

(VI)

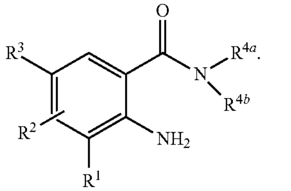

(VII)

2. A process for preparing the compound of formula (I), wherein said process further comprises the step of:

reacting the compound of formula (VII), obtained according to the process of claim 1, with a compound of formula (IX) to obtain a compound of formula (I);

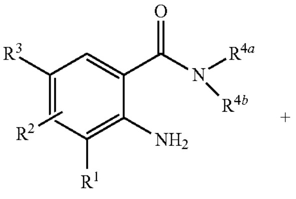

(VII)

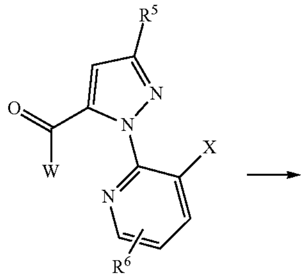

(IX)

-continued

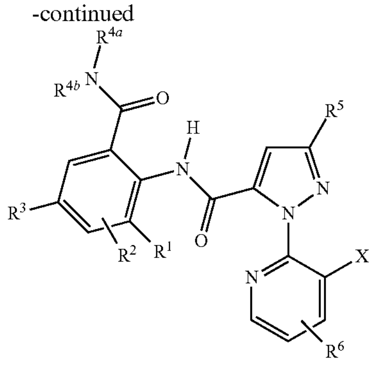

(I)

wherein $R^5$ is selected from the group consisting of halogen, $C_1$-$C_4$ alkyl, $C_1$-$C_4$ haloalkyl, $CHF_2$, $CF_3$, $C_1$-$C_4$ alkoxy; $OCF_2H$, $OCH_2CF_3$, and -A- $C_3$-$C_5$ heterocyclyl;

wherein -A- is selected from the group consisting of direct bond, $CHR^6$, —O— and —S—; and said heterocyclyl may optionally be substituted with one or more group selected from the group consisting of hydrogen, halogen, cyano, $C_1$-$C_4$ alkyl and $C_1$-$C_4$ haloalkyl;

$R^6$ is selected from the group consisting of hydrogen, halogen, cyano, $C_1$-$C_4$ alkyl and $C_1$-$C_4$ haloalkyl;

X is halogen;

W is selected from the group consisting of OH, Cl, O—$C_1$-$C_4$ alkyl, O—C(O)$C_1$-$C_4$ alkyl and imidazolyl;

optionally in the presence of a base, a coupling agent, or i. reacting the compound of formula (VIIa), obtained in step c) with a compound of formula (IX), to obtain a compound of formula (IA),

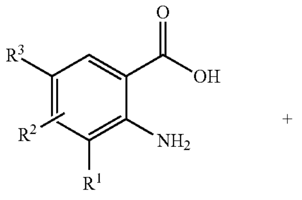

(VIIa)

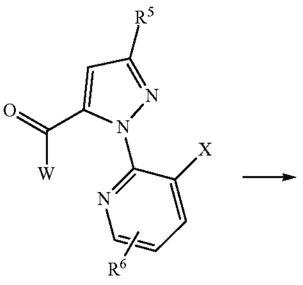

(IX)

-continued

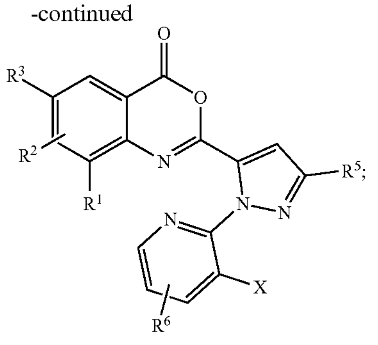

IA and ii. reacting the compound of formula (IA) with a substituted amine of formula (VIII) to obtain a compound of formula (I);

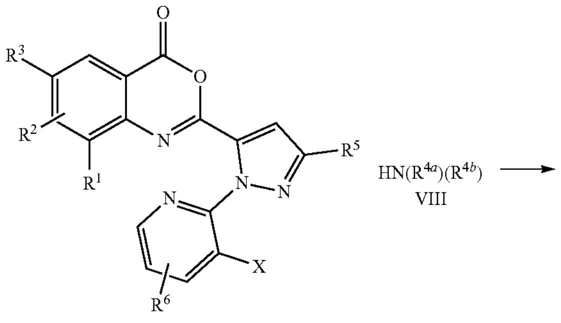

IA

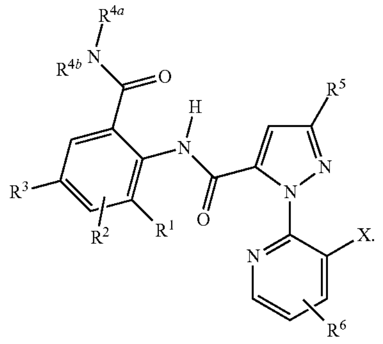

I

3. A process for the synthesis of a compound of formula (V), (V)

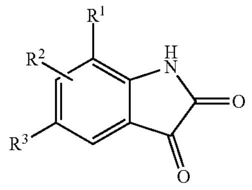

wherein, $R^1$ is selected from the group consisting of halogen, $C_1$-$C_4$ alkyl and $C_3$-$C_4$-cycloalkyl;

$R^2$ is selected from the group consisting of hydrogen, halogen, cyano, $C_1$-$C_4$ alkyl and $C_3$-$C_4$-cycloalkyl;

$R^3$ is selected from the group consisting of hydrogen, halogen, cyano, $C_1$-$C_4$ haloalkyl and $C_3$-$C_6$ cycloalkyl;

comprising the steps of:

a) reacting a compound of formula (II) with a compound of formula (III) to afford a compound of formula (IV), optionally in the presence of a base and a solvent;

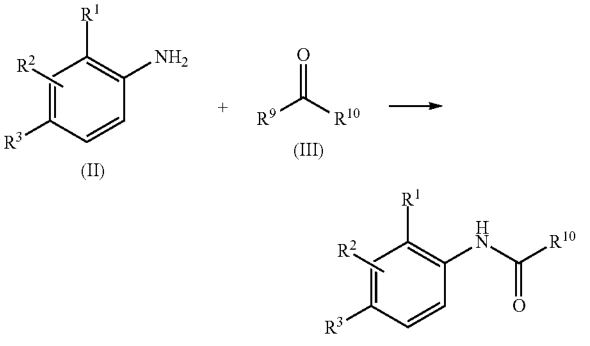

(II) (III) (IV)

wherein, $R^9$ is selected from the group consisting of Cl, Br and $C_1$-$C_4$ alkoxy;

$R^{10}$ is selected from the group consisting of cyano, $CH_2X$, $CH_2$—(C═O)—$OR^a$, —$COOR^a$, $C(O)R^c$ and $CR^d$=$NR^e$;

$R^a$ is selected from the group comprising consisting of hydrogen and $C_1$-$C_4$-alkyl, $R^c$ is selected from the group consisting of $N(R^a)_2$ and two $R^a$ together with the atoms to which they are attached or together with further atoms selected from the group consisting of C, N, O, S and optionally including 1 to 3 ring members selected from the group consisting of C(═O), C(═S), $S(O)_m$ and SiR'2 may form a five to six membered non-aromatic ring;

$R^d$ is selected from the groups consisting of hydrogen and —$C_1$-$C_4$-alkyl, (C═O)—$R^a$, $COOR^a$, $CON(R^a)_2$ and phenyl;

$R^e$ is selected from the groups comprising consisting of hydroxy and $C_1$-$C_4$ alkoxy;

X represents halogen; and b) reacting the compound of formula (IV) with an acid to obtain isatin of formula (V), optionally in the presence of a solvent;

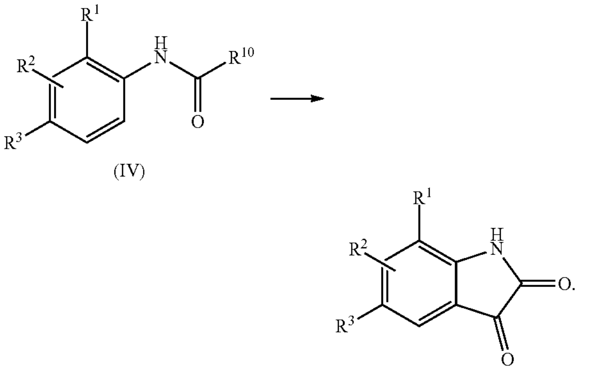

(IV) (V)

4. The process according to claim 3, wherein, said step-a is carried out by one or more steps selected from i-a to v-a i-a reacting a compound of formula (II) with a compound of formula (XII) or a compound of formula (XIII) to obtain a compound of formula (IVa)

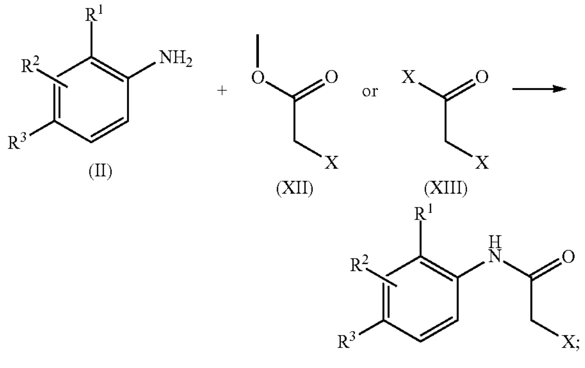

(II) (XII) or (XIII) (IVa)

or ii-a reacting a compound of formula (II) with malonate ester of formula (IIIa) $CH_2(COOC_1$-$C_2$ alkyl$)_2$ to a obtain compound of formula (IVc);

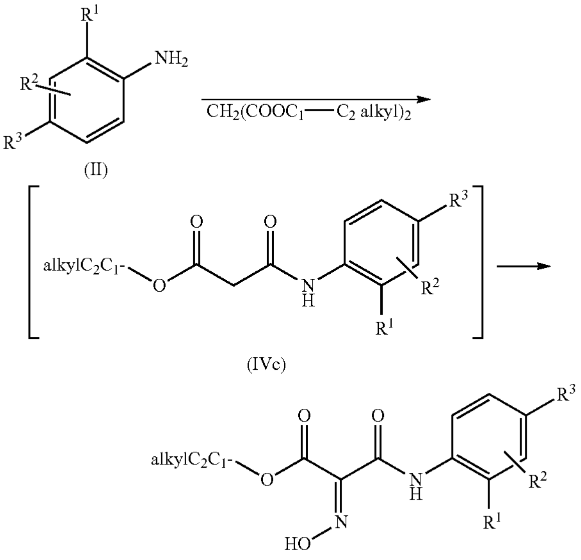

(II) (IVc) (IVd)

and optionally isolating the compound of formula (IVc) or further reacting the compound of formula (IVc) with an inorganic nitrite reagent and an acid or an organic nitrite reagents to obtain a compound of formula (IVd),

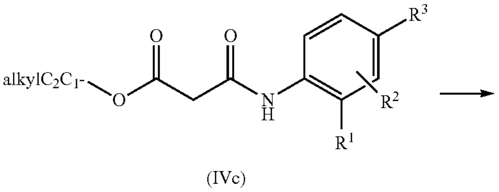

(IVc)

-continued

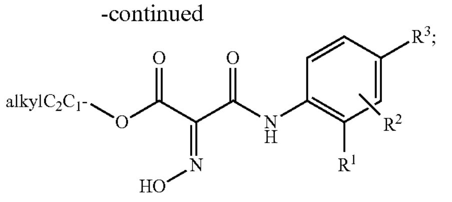

(IVd)

or iii-a reacting a compound of formula (IVf) with amine of formula N ($R^a$) 2 to obtain a compound of formula (IVg)

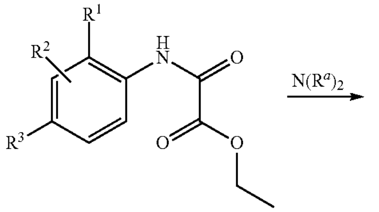

(IVf)

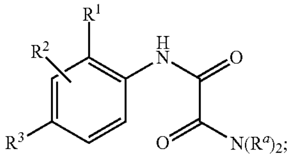

(IVg)

or iv-a reacting a compound of formula (IVf) with ammonia to obtain a compound of formula (IVh)

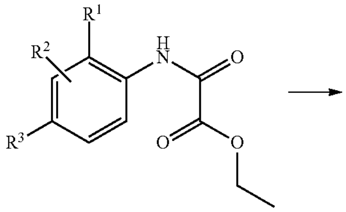

(IVf)

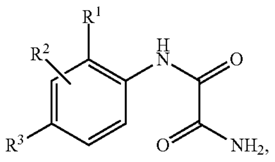

(IVh)

and reacting compound of formula (IVh) with reagent-2 to obtain a compound of formula (IVi)

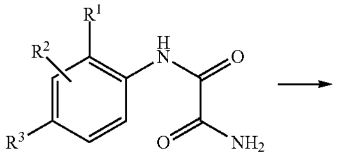

(IVh)

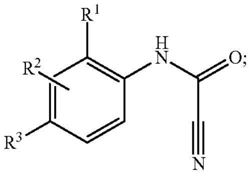

(IVi)

or v-a reacting a compound of formula (II) with a compound of formula (X) or a compound of formula (XI) to obtain a compound of formula (IVj)

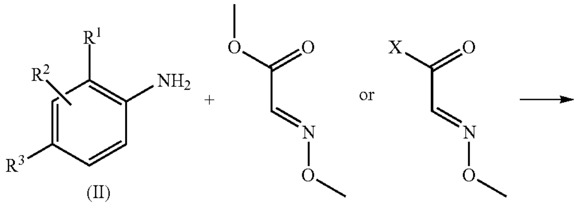

(II) (X) (XI)

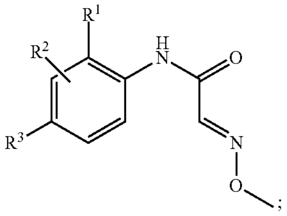

(IVj)

wherein $R^3$ is hydrogen.

5. The process according to claim 3, wherein, said step-b is carried out by one or more steps selected from i-b to v-b i-b reacting the compound of formula (IVa) with hydroxyl amine derivative using a base to obtain a compound of formula (IVb)

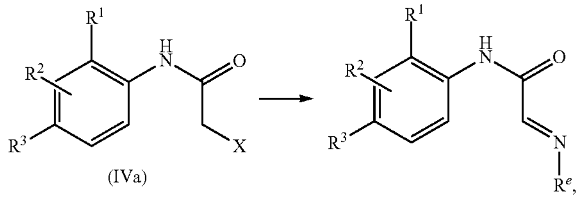

(IVa) (IVb)

and further reacting compound of formula (IVb) with an acid to obtain isatin of formula (V)

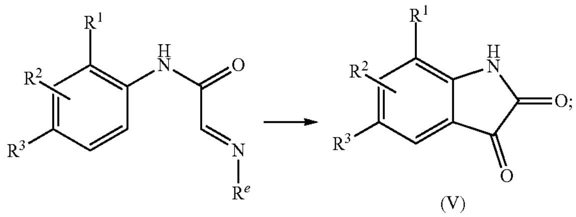

(IVb) (V)

or ii-b reacting compound of formula (IVd) with a base to obtain a compound of formula (IVe)

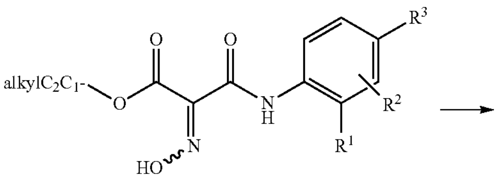

(IVd)

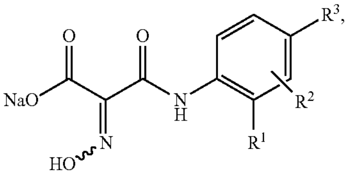

(IVe)

and optionally isolating compound of formula (IVe) or reacting compound of formula (IVe) with an acid to obtain isatin of formula (V)

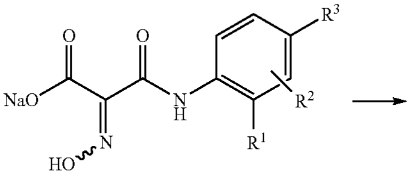

(IVe)

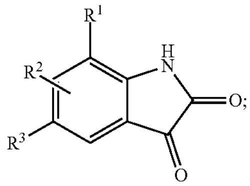

(V)

or iii-b reacting compound of formula (IVi) with a Lewis acid to obtain isatin formula (V)

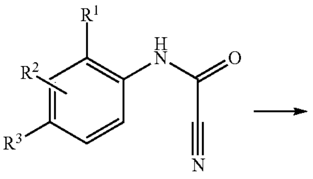

(IVi)

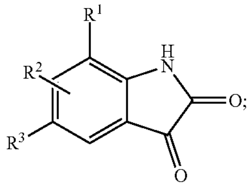

(V)

or iv-b reacting the compound of formula (IVg) with a reagent-2 to obtain isatin of formula (V)

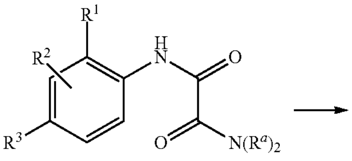

(IVg)

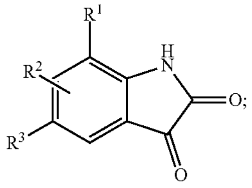

(V)

or v-b reacting compound of formula (IVj) with an acid to obtain isatin of formula (V)

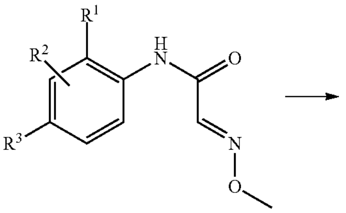

(IVj)

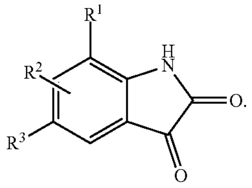

(V)

6. The process according to claim 3, wherein said process further comprises the step of:

hydrolyzing isatin of formula (V) to obtain an anthranilic acid of formula (VIIa) in the presence of a hydrolyzing agent, optionally in the presence of a solvent;

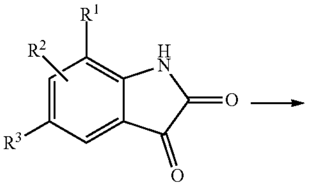

(V)

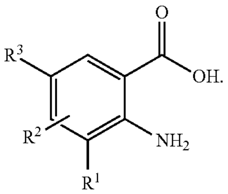

(VIIa)

7. The process according to claim 1, wherein, said process for the synthesis of a compound of (VII), (VII)

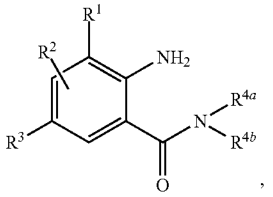

from compound of formula (IVa), (IVa)

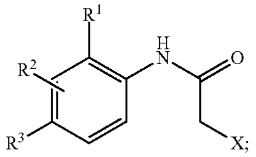

comprising the steps of:

A-1. reacting the compound of formula (II) with compound of formula (XII) or compound of formula (XIII) to obtain a compound of formula (IVa)

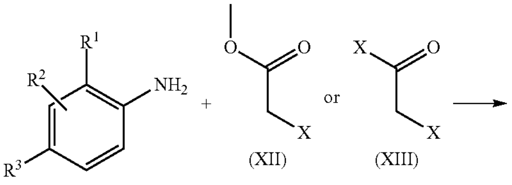

(II) (XII) or (XIII)

-continued

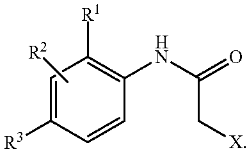

(IVa)

B-1. converting the compound of formula (IVa) to a compound of formula (IVb) by reacting it with a hydroxyl amine derivative in the presence of a base and a solvent:

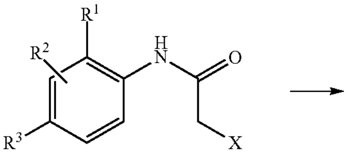

(IVa)

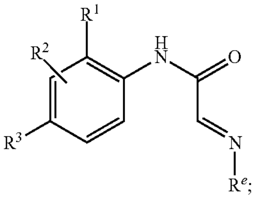

(IVb)

C-1. converting the compound of formula (IVb) to isatin of formula (V) by reacting it with sulphuric acid in the presence of a solvent

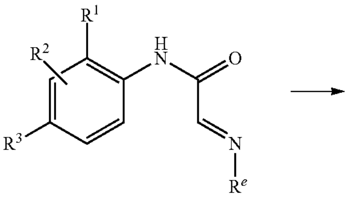

(IVb)

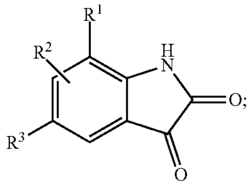

(V)

D-1. oxidising isatin of formula (V) using an oxidizing agent in the presence of a catalyst to obtain a compound of formula (VI);

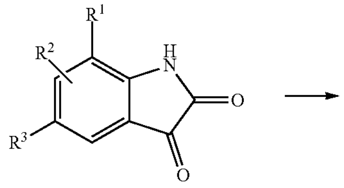

(V)

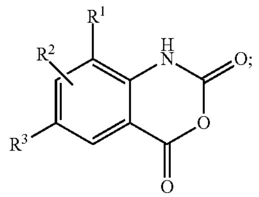

(VI)

and

E-1. reacting the compound of formula (VI) with a compound of formula (VIII), to obtain a compound of formula (VII), optionally in the presence of an acid and a solvent;

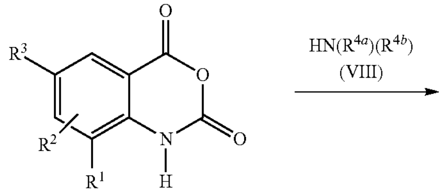

(VI)

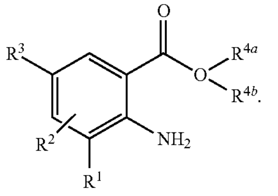

(VII)

8. The process according to claim 1, wherein, said process for the synthesis of a compound of (VII), (VII)

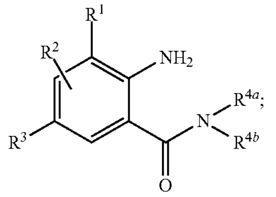

from the compound of formula (II), (II)

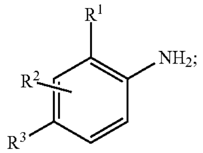

comprising the steps of:

A-2. reacting the compound of formula (II) with a malonate ester of formula $CH_2(COOC_1\text{-}C_2\ alkyl)_2$ IIIa to obtain a compound of formula (IVc) that can be optionally isolated and subsequently converted to the compound of formula (IVd) by reacting it with an inorganic nitrite in the presence of an acid, or with an organic nitrite in the presence of a solvent;

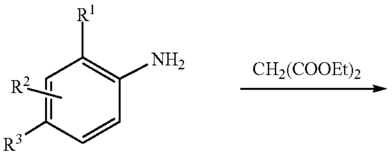

(II)

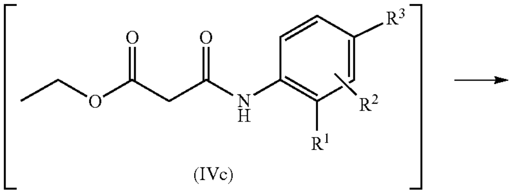

(IVc)

Isolation is optional

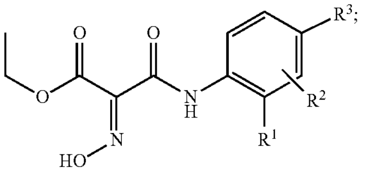

(IVd)

B-2. reacting the compound of formula (IVd) with a base, optionally in the presence of a solvent to obtain intermediate of formula (IVe) that can be optionally isolated and further treated with sulphuric acid, optionally in the presence of a solvent to obtain a compound of formula (V);

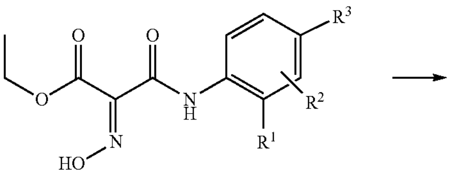

(IVd)

-continued

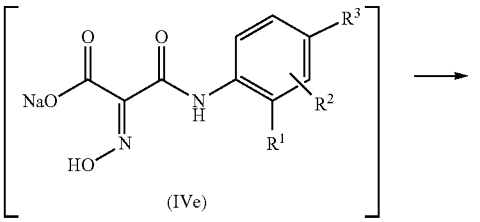

(IVe)

Isolation is optional

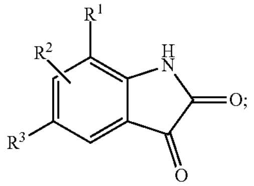

(V)

C-2. oxidising isatin of formula (V) using a oxidizing agent in the presence of a catalyst to obtain compound of formula (VI);

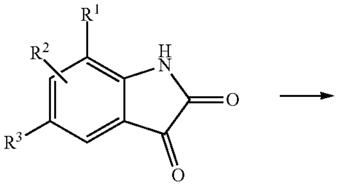

(V)

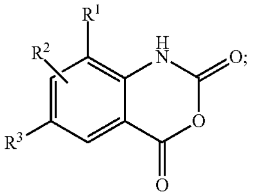

(VI)

and

D-2. reacting the compound of formula (VI) with a compound of formula (VIII), to obtain a compound of formula (VII), optionally in the presence of an acid and a solvent;

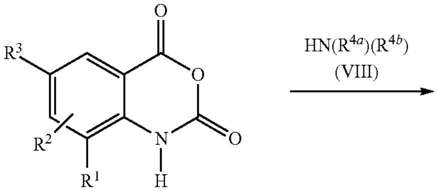

(VI)

-continued

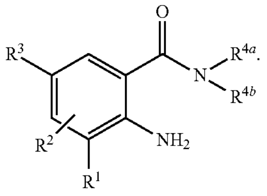

(VII)

9. The process according to claim 1, wherein, said process for the preparation of a compound of formula (VII), (VII)

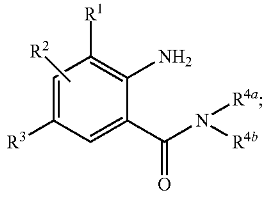

from the compound of formula (IVf), (IVf)

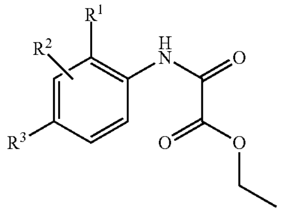

comprising the steps of:

A-3. reacting the compound of formula (IVf) with amine of formula $NH(R^a)_2$, optionally in the presence of a solvent; to obtain a compound of formula (IVg);

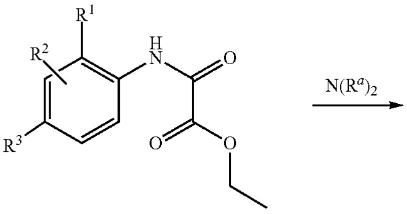

(IVf)

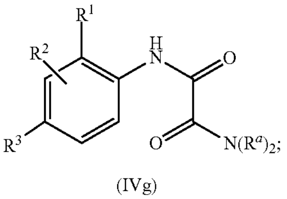

(IVg)

B-3. the compound of formula (IVg) is converted to the compound of formula (V) by reacting with a reagent-2 at a suitable temperature;

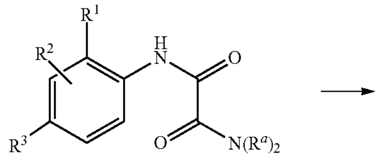

(IVg)

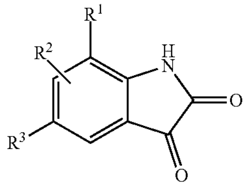

(V)

C-3. oxidising isatin of formula (V) using an oxidizing agent and in the presence of a catalyst to obtain compound of formula (VI);

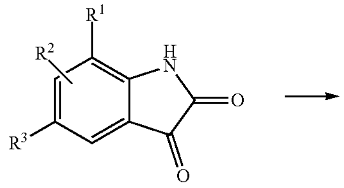

(V)

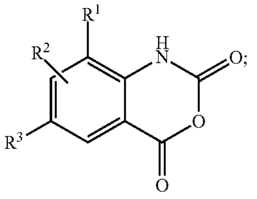

(VI)

and

D-3. reacting the compound of formula (VI) with a compound of formula (VIII), to obtain a compound of formula (VII), optionally in the presence of an acid and a solvent;

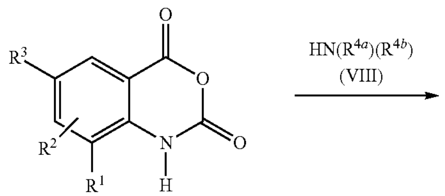

(VI)

-continued

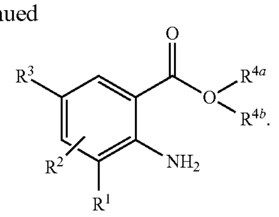

(VII)

10. The process according to claim 1, wherein, $R^1$ is methyl or halogen;

$R^2$ is hydrogen or halogen;

$R^3$ is halogen or cyano;

$R^9$ hydrogen, methyl, ethyl n-propyl, iso-propyl, iso-butyl, tert-butyl;

$R^{4a}$ is methyl, ethyl, n-propyl, iso-propyl, cyclopropyl methylcyclopropyl, ethylcyclopropyl, iso-butyl, tert-butyl;

$R^{4b}$ is hydrogen or methyl;

X is halogen.

11. The process according to claim 1, wherein, $R^1$ is methyl, chloro or bromo;

$R^2$ is hydrogen or fluoro;

$R^3$ is chloro, bromo or cyano;

X is halogen.

12. The process according to claim 2, wherein, $R^1$ is methyl or halogen;

$R^2$ is hydrogen or halogen;

$R^3$ is halogen or cyano;

$R^9$ hydrogen, methyl, ethyl n-propyl, iso-propyl, iso-butyl, tert-butyl;

$R^{4a}$ is methyl, ethyl, n-propyl, iso-propyl, cyclopropyl methylcyclopropyl, ethylcyclopropyl, iso-butyl or tert-butyl;

$R^{4b}$ is hydrogen or methyl;

$R^5$ is selected from the group consisting of bromo, chloro, and -A- $C_3$-$C_5$ heterocyclyl;

wherein -A- is selected from the group consisting of direct bond, $CHR_6$, —O— and —S—; and said heterocyclyl may optionally be substituted with one or more group selected from hydrogen, halogen, cyano, $C_1$-$C_4$ alkyl and $C_1$-$C_4$ haloalkyl;

$R^6$ is selected from the group consisting of hydrogen, halogen, cyano, $C_1$-$C_4$ alkyl and $C_1$-$C_4$ haloalkyl.

13. The process according to claim 2, wherein, $R^1$ is methyl, chloro or bromo;

$R^2$ is hydrogen or fluoro;

$R^3$ is chloro, bromo or cyano;

$R^5$ is selected from the group consisting of bromo, chloro and

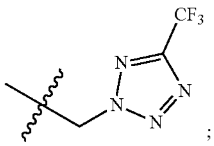 [SMILES: *Cn1nnc(C(F)(F)F)n1]

;

$R^6$ is selected from the group consisting of hydrogen, bromo, chloro er and fluoro.

14. The process according to claim 2, wherein compound of formula (I) is selected from the group consisting of chlorantraniliprole, cyantraniliprole, cyclaniliprole, tetraniliprole, tetra-chlorantraniliprole, bromantraniliprole and fluchlordiniliprole.

15. The process as claimed in claim 3, wherein the said process comprises the steps of:

reacting compound of formula (IVa-1) with a Lewis acid to obtain compound of formula (Va)

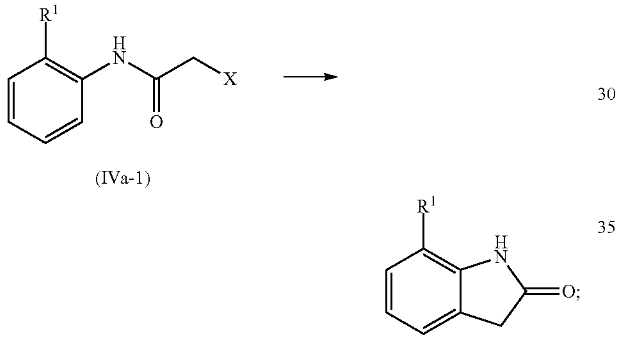

(IVa-1) (Va)

halogenating compound of formula (Va) to obtain compound of formula (Vb)

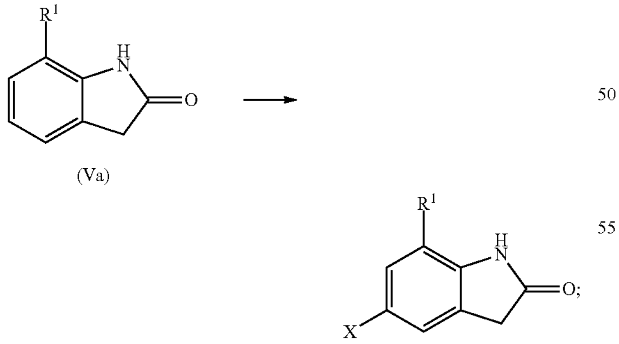

(Va) (Vb)

further, oxidizing compound of formula (Vb) using an oxidizing agent and a catalyst to obtain compound of formula (Vc) or converting compound of formula (Vc) to a compound of formula (Vd) using an oxidizing agent and a catalyst, further, reacting compound of formula (Vc) or compound of formula (Vd) with an acid or a base to obtain compound of formula (VIIa)

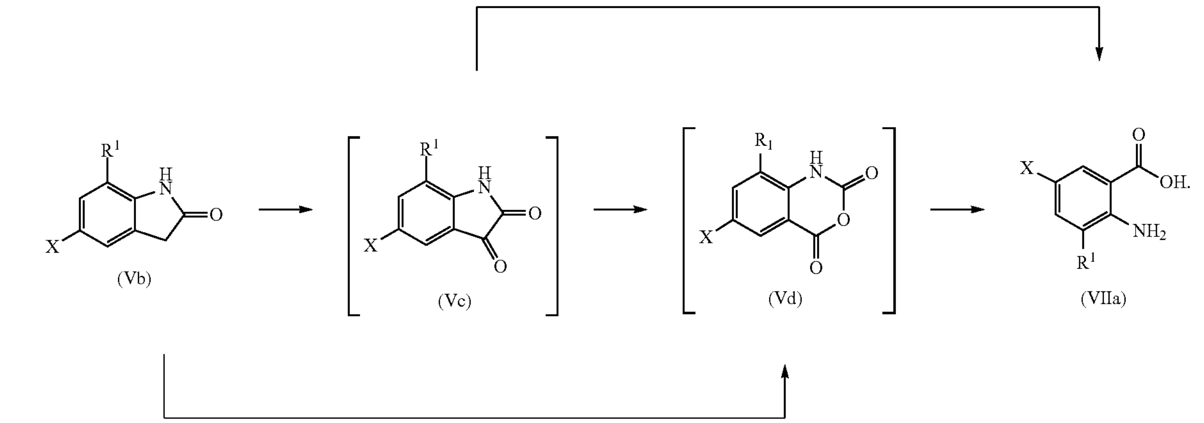

(Vb) (Vc) (Vd) (VIIa)

16. The process according to claim 1, wherein said acid is selected from hydrochloric acid, hydrobromic acid, sulfuric acid, formic acid, acetic acid, trifluoroacetic acid, propionic acid, methanesulfonic acid, benzenesulfonic acid, p-toluenesulfonic acid, an acidic ion-exchange resin and mixtures thereof.

17. The process according to claim 1, wherein said suitable base is selected from ammonia, alkali or alkaline earth metal hydroxide or carbonate or bicarbonate, methylamine, dimethyl amine, diethyl amine, triethyl amine, diisopropylamine, diisopropyl ethyl amine, pyridine, alkylated and dialkylated pyridines, dimethylamino pyridine, piperidine and mixtures thereof.

18. The process according to claim 15, wherein said suitable halogenating reagent is selected from HX, $CuX_2$, $MgX_2$, CsX, $ZnX_2$, $SOCl_2$, $SO_2Cl_2$, $COCl_2$, $X_2$, $C(=O)(OCl_3)_2$, t-BuOCl, NaOCl, chloramine-T, N-halosuccinamides, $POX_3$, $PX_3$, $PX_5$ and metal halides; wherein X is Cl, Br, I and F.

19. The process as claimed in claim 1, wherein said reaction steps are carried out using suitable solvent selected from chlorobenzene, dichlorobenzene, dichloromethane, chloroform, tetrachloromethane, dichloroethane, trichloroethane, diethylether, diisopropyl ether, methyl tert-butyl ether, methyl tert-amyl ether, dioxane, tetrahydrofuran, 1,2-dimethoxy ethane, 1,2-diethoxyethane, anisole, acetonitrile, propionitrile, n- or iso-butyronitrile, benzonitrile, ethyl acetate, N,N-dimethylformamide, N,N-dimethylacetamide, N-methylformanilide, N-methylpyrrolidone, hexamethylphosphoric triamide, dimethyl sulfoxide, sulfones, sulfolane, methanol, ethanol, n- or i-propanol, n-, i-, sec- or tert-butanol, water and mixtures thereof.

20. The process as claimed in claim 2, wherein said suitable coupling reagent is selected from I-(3-dimethylaminopropyl)-3-ethylcarbodiimide hydrochloride (EDC), dicyclohexylcarbodiimide (DCC), I-cyclohexyl-3-(2-morpholmoethyl) carbodiimide, 1,3-di-tert-butylcarbodiimide, I-(dimethylaminopropyl)-3-ethylcarbodiimide methiodide, I-tert-butyl-3-(1liphenylmethyl)-carbodiimide, 1,3-diisopropylcarbodiimide, bis-(diphenylmethyl)-carbodiimide, I-tert-butyl-3-ethylcarbodiimide, 1-methyl-2-chloropyridinium iodide, 2-ethoxy-I-ethoxycarbonyl-1,2-dihydroquinoline (EEDQ), BOP-chloride and isobutyl chloroformate.

21. The process as claimed in claim 15, wherein said Lewis acid is selected from $AlX_3$, $BX_3$, $FeX_3$, $ZnX_2$, $GaX_3$, $InX_3$, $TiX_4$, $BiX_3$, $SbX_3$, $SnX_2$, $SnX_4$, $SiX_4$, and hypovalent Lewis acids, wherein X is halogen.

22. The process as claimed in claim 1, wherein said oxidizing agent is selected from hydrogen peroxide, oxone, hydrogen peroxide, t-butyl-hydroperoxide, tungstic peroxide, m-chloroperbenzoic acid, benzoyl peroxide, hypohalous acid, ceric ammonium nitrate, oxone, Sodium (meta) periodateperiodic acid, peracetic acid, performic acid hydrogen peroxide urea-adduct, sodium perborate, pyridinium chlorochromate, Ruthenium (II) oxide, Manganese (II) oxide, Copper (II) acetate/$O_2$ and dimethyl sulfoxide.

23. The process as claimed in claim 1, wherein said catalyst is selected from selenic acid, selenous acid, selenium dioxide.

* * * * *